(12) United States Patent
O'Connor et al.

(10) Patent No.: US 12,611,322 B2
(45) Date of Patent: Apr. 28, 2026

(54) DEVICE AND METHOD FOR COMPRESSING AND LOADING A STENT

(71) Applicant: BOSTON SCIENTIFIC SCIMED, INC., Maple Grove, MN (US)

(72) Inventors: Tim O'Connor, Galway (IE); Declan Loughnane, Galway (IE); John Lardner, Galway (IE); Pearse A. Coffey, Galway (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 778 days.

(21) Appl. No.: 17/964,460

(22) Filed: Oct. 12, 2022

(65) Prior Publication Data

US 2023/0111435 A1 Apr. 13, 2023

Related U.S. Application Data

(60) Provisional application No. 63/255,101, filed on Oct. 13, 2021.

(51) Int. Cl.
| | |
|---|---|
| *A61F 2/95* | (2013.01) |
| *A61F 2/00* | (2006.01) |
| *A61F 2/24* | (2006.01) |

(52) U.S. Cl.
CPC .......... *A61F 2/9525* (2020.05); *A61F 2/0095* (2013.01); *A61F 2/243* (2013.01); *A61F 2/9524* (2020.05)

(58) Field of Classification Search
CPC .... A61F 2/9525; A61F 2/9524; A61F 2/9522; B23P 11/005
See application file for complete search history.

(56) References Cited

U.S. PATENT DOCUMENTS

| | | | |
|---|---|---|---|
| 1,055,825 | A | 3/1913 | Snyder |
| 6,823,576 | B2 | 11/2004 | Austin |

(Continued)

FOREIGN PATENT DOCUMENTS

| | | | | |
|---|---|---|---|---|
| EP | 3360514 A1 * | 8/2018 | .......... | A61F 2/9522 |
| EP | 3498223 A1 * | 6/2019 | .......... | A61F 2/9522 |

(Continued)

OTHER PUBLICATIONS

International Search Report and Written Opinion dated Feb. 1, 2023 for International Application No. PCT/US2022/046410.
U.S. Appl. No. 17/963,560, filed Oct. 11, 2022.

*Primary Examiner* — Alvin J Stewart
(74) *Attorney, Agent, or Firm* — Seager, Tufte & Wickhem LLP

(57) ABSTRACT

A device for compressing a stent may include a housing extending along a central longitudinal axis, a first threaded member and a second threaded member, a first iris and a second iris, and a compressor element disposed between the second iris and the second threaded member. The first iris includes a first ring extending transverse to the axis and a first plurality of arms extending from the first ring parallel to the axis. The first plurality of arms defines a first central opening and rotation of the first threaded member changes a size of the first central opening. The second iris includes a second ring extending transverse to the axis and a second plurality of arms extending from the second ring parallel to the axis. The second plurality of arms defines a second central opening and rotation of the second threaded member changes a size of the second central opening.

12 Claims, 14 Drawing Sheets

(56)　　　References Cited

U.S. PATENT DOCUMENTS

| | | | |
|---|---|---|---|
| 7,578,041 | B2 | 8/2009 | Weber et al. |
| 8,006,535 | B2 * | 8/2011 | Righini ................. A61F 2/2415 |
| | | | 72/402 |
| 8,011,078 | B2 | 9/2011 | Pacetti |
| 8,221,824 | B2 | 7/2012 | Timm |
| 8,291,570 | B2 | 10/2012 | Eidenschink et al. |
| 8,333,000 | B2 | 12/2012 | Huang et al. |
| 8,474,122 | B2 | 7/2013 | Melsheimer |
| 8,544,160 | B2 | 10/2013 | Kokish et al. |
| 8,595,913 | B2 | 12/2013 | Knott et al. |
| 8,632,847 | B2 | 1/2014 | Pacetti |
| 8,752,261 | B2 | 6/2014 | Van Sciver |
| 8,931,159 | B2 * | 1/2015 | Hillukka ............... A61F 2/2418 |
| | | | 623/2.11 |
| 9,125,763 | B2 | 9/2015 | Wang et al. |
| 9,138,338 | B2 | 9/2015 | Chambers et al. |
| 9,895,241 | B2 | 2/2018 | Wang |
| 10,010,412 | B2 * | 7/2018 | Taft ............................ A61F 2/95 |
| 10,245,145 | B2 * | 4/2019 | Mantanus ............. A61F 2/2436 |
| 10,292,844 | B2 | 5/2019 | Orth et al. |
| 10,307,277 | B2 | 6/2019 | Wang |
| 10,335,270 | B2 * | 7/2019 | Essinger ............... A61F 2/2418 |
| 10,357,363 | B2 | 7/2019 | Frisby |
| 10,660,773 | B2 | 5/2020 | Wang et al. |
| 10,682,228 | B2 * | 6/2020 | Mantanus ............. A61F 2/2436 |
| 10,722,357 | B2 * | 7/2020 | High ..................... A61F 2/2418 |
| 10,918,478 | B2 | 2/2021 | Taft et al. |
| 10,967,556 | B2 | 4/2021 | Wang et al. |
| 11,786,372 | B2 * | 10/2023 | Mantanus ............. A61F 2/2436 |
| | | | 29/446 |
| 2014/0215791 | A1 * | 8/2014 | Soundararajan ...... A61F 2/9524 |
| | | | 29/700 |
| 2015/0107078 | A1 * | 4/2015 | Jahn ..................... A61F 2/9526 |
| | | | 29/700 |
| 2019/0021834 | A1 * | 1/2019 | Nir ........................ A61F 2/0095 |
| 2019/0053900 | A1 * | 2/2019 | Finn ..................... A61F 2/2436 |
| 2020/0205971 | A1 | 7/2020 | Mantanus et al. |
| 2022/0362042 | A1 * | 11/2022 | Fox ....................... A61F 2/9525 |
| 2023/0255758 | A1 * | 8/2023 | Taft ...................... A61F 2/2433 |
| | | | 606/1 |
| 2024/0225830 | A1 * | 7/2024 | Frisby ................... A61F 2/9525 |

FOREIGN PATENT DOCUMENTS

| | | | | | |
|---|---|---|---|---|---|
| EP | | 4374831 | A1 * | 5/2024 | .......... A61F 2/9525 |
| WO | | WO-2013016549 | A1 * | 1/2013 | .......... A61F 2/2433 |
| WO | | WO-2018064690 | A1 * | 4/2018 | .............. A61F 2/95 |
| WO | | 2021127180 | A1 | 6/2021 | |
| WO | | WO-2022266164 | A1 * | 12/2022 | .......... A61F 2/9525 |
| WO | | WO-2023287752 | A1 * | 1/2023 | .......... A61F 2/2418 |
| WO | | WO-2023064362 | A1 * | 4/2023 | .......... A61F 2/9525 |
| WO | | WO-2023076103 | A1 * | 5/2023 | ............. A61F 2/243 |
| WO | | WO-2023114817 | A1 * | 6/2023 | .......... A61F 2/9525 |
| WO | | WO-2023156307 | A1 * | 8/2023 | ............. A61F 2/95 |
| WO | | WO-2023164239 | A1 * | 8/2023 | .......... A61F 2/2418 |
| WO | | WO-2025029333 | A1 * | 2/2025 | .......... A61F 2/2418 |
| WO | | WO-2025042676 | A1 * | 2/2025 | .......... A61F 2/9522 |

* cited by examiner

100

120

110

140

130

DEVICE AND METHOD FOR COMPRESSING AND LOADING A STENT

CROSS-REFERENCE TO RELATED APPLICATIONS

This application claims the benefit of priority of U.S. Provisional Application No. 63/255,101 filed Oct. 13, 2021, the entire disclosure of which is hereby incorporated by reference.

TECHNICAL FIELD

The present disclosure pertains to medical devices, systems, and methods for manufacturing and/or using medical devices and/or systems. More particularly, the present disclosure pertains to a device and/or method for radially compressing and/or loading a stent and/or a stent device such as a replacement heart valve implant.

BACKGROUND

Conventional stent crimping devices have been used throughout the medical device industry to crimp balloon expandable stents, self-expanding stents, replacement heart valve implants, etc. Conventional stent crimping devices have complex arrangements of multiple parts and/or difficult assemblies and rely upon complex interactions between many moving parts. The cost of a conventional stent crimping device may be significant due to the aforementioned complexity and number of components. In some cases, the process of sheathing a stent may be complex and/or involve numerous steps that must be repeated along the length of the stent. Of the known devices and methods, each has certain advantages and disadvantages. There is an ongoing need for alternative devices and/or methods for compressing stents, stent devices, and/or other medical implants that may include a stent, such as but not limited to replacement heart valve implants.

SUMMARY

In one example, a device for radially compressing a stent may comprise a housing extending along a central longitudinal axis, a first threaded member configured to engage the housing, a first iris positioned adjacent the housing, and a loading funnel removably coupled to the housing, the loading funnel having an inner surface that is tapered radially inward toward the first iris. The first iris includes a first circumferential ring extending transverse to the central longitudinal axis and a first plurality of arms extending from the first circumferential ring in a first direction parallel to the central longitudinal axis. The first plurality of arms defines a first central opening positioned coaxially relative to the central longitudinal axis. Rotation of the first threaded member relative to the housing changes a size of the first central opening.

In addition or alternatively to any example described herein, the first threaded member is configured to engage the first plurality of arms.

In addition or alternatively to any example described herein, each of the first plurality of arms includes a first tapered surface configured to engage a first angled surface defining a first central aperture of the first threaded member.

In addition or alternatively to any example described herein, the first plurality of arms is configured to deflect radially between a first configuration and a second configuration upon rotation of the first threaded member relative to the housing.

In addition or alternatively to any example described herein, the first plurality of arms is configured to deflect toward the second configuration upon clockwise rotation of the first threaded member relative to the housing.

In addition or alternatively to any example described herein, the first plurality of arms is configured to deflect toward the first configuration upon counterclockwise rotation of the first threaded member relative to the housing.

In addition or alternatively to any example described herein, the first plurality of arms is monolithically formed with the first circumferential ring from a single piece of material.

In addition or alternatively to any example described herein, the single piece of material is formed from a polymeric material.

In addition or alternatively to any example described herein, a device for radially compressing a stent may comprise a housing extending along a central longitudinal axis, a first threaded member configured to engage the housing, a second threaded member configured to engage the housing, a first iris positioned adjacent the housing, a second iris positioned adjacent the housing, and a compressor element disposed between the second iris and the second threaded member. The first iris includes a first circumferential ring extending transverse to the central longitudinal axis and a first plurality of arms extending from the first circumferential ring in a first direction parallel to the central longitudinal axis. The first plurality of arms defines a first central opening positioned coaxially relative to the central longitudinal axis. Rotation of the first threaded member relative to the housing changes a size of the first central opening. The second iris includes a second circumferential ring extending transverse to the central longitudinal axis and a second plurality of arms extending from the second circumferential ring in a second direction parallel to the central longitudinal axis. The second plurality of arms defines a second central opening positioned coaxially relative to the central longitudinal axis. Rotation of the second threaded member relative to the housing changes a size of the second central opening.

In addition or alternatively to any example described herein, the second threaded member is configured to engage the compressor element and the compressor element is configured to engage the second plurality of arms.

In addition or alternatively to any example described herein, each of the second plurality of arms includes a second tapered surface configured to engage a second angled surface defining a second central aperture of the compressor element.

In addition or alternatively to any example described herein, the second iris is axially offset from the first iris.

In addition or alternatively to any example described herein, the first threaded member and the second threaded member are rotatable relative to the housing independently of each other.

In addition or alternatively to any example described herein, a first portion of the compressor element is disposed radially outward of the housing and a second portion of the compressor element is disposed radially inward of the housing.

In addition or alternatively to any example described herein, a method of radially compressing a stent may comprise:

inserting a stent in a first configuration through a loading funnel removably coupled to a housing into a first central opening of a first iris positioned adjacent the housing;

wherein the first iris includes a first circumferential ring extending transverse to a central longitudinal axis of the housing, and a first plurality of arms extending from the first circumferential ring in a first direction parallel to the central longitudinal axis and defining the first central opening; and rotating a first threaded member relative to the housing to shift the first plurality of arms from a first configuration to a second configuration, wherein the first central opening has a first size in the first configuration and a second size in the second configuration less than the first size;

wherein in the second configuration of the first plurality of arms, a first portion of the stent disposed within the first iris is in a radially compressed configuration.

In addition or alternatively to any example described herein, the method may comprise:

positioning a sheath proximate the first iris with the first plurality of arms in the second configuration and the first portion of the stent disposed within the first iris in the radially compressed configuration;

rotating the first threaded member relative to the housing to shift the first plurality of arms from the second configuration to the first configuration; and moving the sheath into the first iris over the stent such that the first portion of the stent that was disposed within the first iris is disposed within the sheath.

In addition or alternatively to any example described herein, the sheath has an inner diameter less than an outer diameter of the stent in the first configuration.

In addition or alternatively to any example described herein, inserting the stent further includes inserting the stent in the first configuration into the first iris and a second iris axially offset from the first iris, wherein the second iris includes a second circumferential ring extending transverse to the central longitudinal axis and a second plurality of arms extending from the second circumferential ring in a second direction parallel to the central longitudinal axis and defining a second central opening.

In addition or alternatively to any example described herein, the method may comprise:

rotating a second threaded member relative to the housing to shift the second plurality of arms from a first configuration to a second configuration, wherein the second central opening has a first size in the first configuration and a second size in the second configuration less than the first size;

wherein in the second configuration of the second plurality of arms, a second portion of the stent disposed within the second iris is in the radially compressed configuration.

In addition or alternatively to any example described herein, the method may comprise:

positioning a sheath proximate the first iris with the first plurality of arms in the second configuration and the first portion of the stent disposed within the first iris in the radially compressed configuration;

rotating the first threaded member relative to the housing to shift the first plurality of arms from the second configuration to the first configuration;

moving the sheath into the first iris over the stent such that the first portion of the stent that was disposed within the first iris is disposed within the sheath;

rotating the second threaded member relative to the housing to shift the second plurality of arms from the second configuration to the first configuration; and moving the sheath into the second iris over the stent such that the second portion of the stent that was disposed within the second iris is disposed within the sheath.

The above summary of some embodiments, aspects, and/or examples is not intended to describe each disclosed embodiment or every implementation of the present disclosure. The figures and detailed description which follow more particularly exemplify these embodiments.

BRIEF DESCRIPTION OF THE DRAWINGS

The disclosure may be more completely understood in consideration of the following detailed description in connection with the accompanying drawings, in which.

Figure 1A:
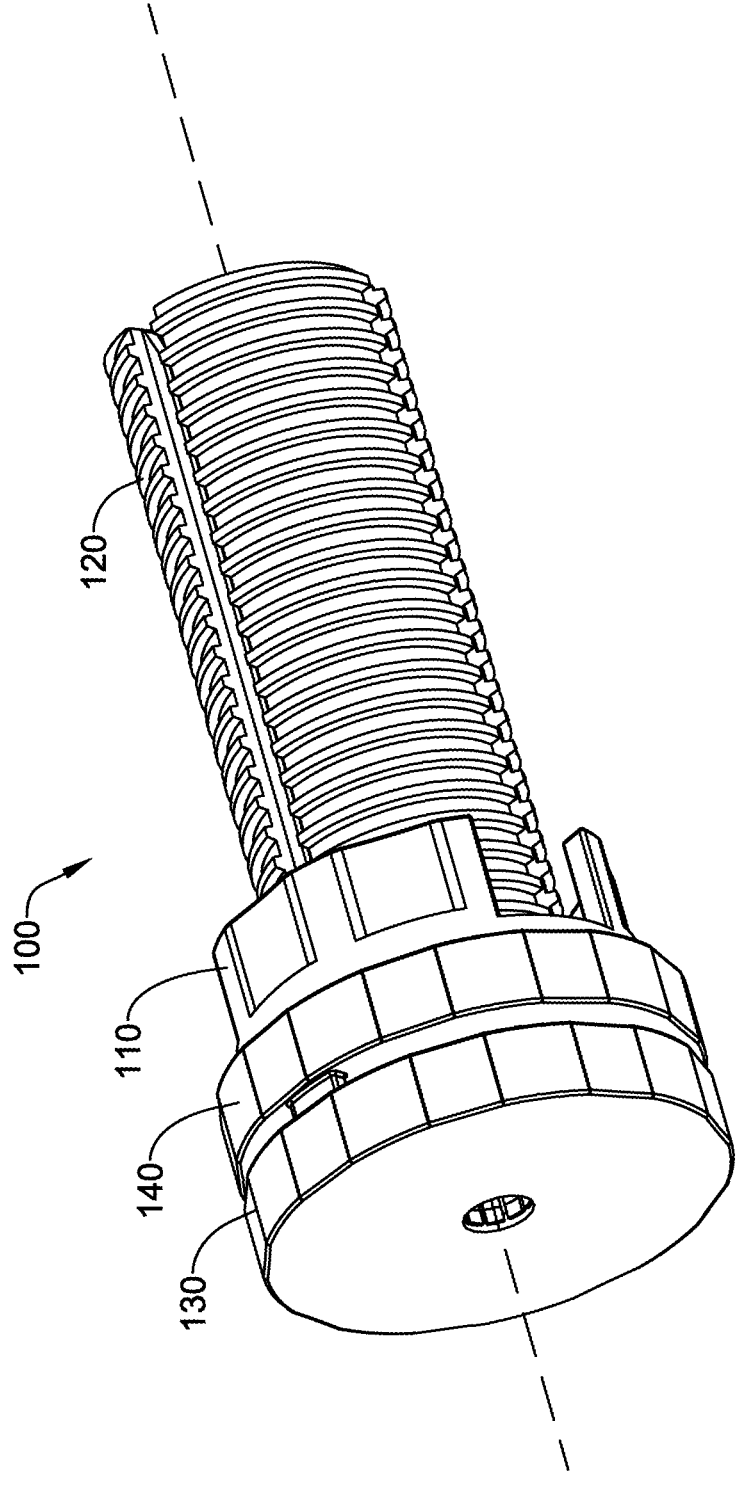
FIGS. 1A-1B are different perspective views illustrating selected aspects of a device for radially compressing a stent.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate example embodiments of the disclosure but not limit the disclosure. Those skilled in the art will recognize that the various elements described and/or shown may be arranged in various combinations and configurations without departing from the scope of the disclosure. However, in the interest of clarity and ease of understanding, every feature and/or element may not be shown in each drawing.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosure are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Still other relative terms, such as "axial", "circumferential", "longitudinal", "lateral", "radial", etc. and/or variants thereof generally refer to direction and/or orientation relative to a central longitudinal axis of the disclosed structure or device.

The term "extent" may be understood to mean the greatest measurement of a stated or identified dimension, unless the extent or dimension in question is preceded by or identified as a "minimum", which may be understood to mean the smallest measurement of the stated or identified dimension. For example, "outer extent" may be understood to mean an outer dimension, "radial extent" may be understood to mean a radial dimension, "longitudinal extent" may be understood to mean a longitudinal dimension, etc. Each instance of an "extent" may be different (e.g., axial, longitudinal, lateral, radial, circumferential, etc.) and will be apparent to the skilled person from the context of the individual usage. Generally, an "extent" may be considered the greatest possible dimension measured according to the intended usage, while a "minimum extent" may be considered the smallest possible dimension measured according to the intended usage. In some instances, an "extent" may generally be measured orthogonally within a plane and/or cross-section, but may be, as will be apparent from the particular context, measured differently-such as, but not limited to, angularly, radially, circumferentially (e.g., along an arc), etc.

The terms "monolithic" and "unitary" shall generally refer to an element or elements made from or consisting of a single structure or base unit/element. A monolithic and/or unitary element shall exclude structure and/or features made by assembling or otherwise joining multiple discrete structures or elements together.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to use the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For example, a reference to "the arm", "the iris", "the threaded member", or other features may be equally referred to all instances and quantities beyond one of said feature unless clearly stated to the contrary. As such, it will be understood that the following discussion may apply equally to any and/or all of the components for which there are more than one within the device, etc. unless explicitly stated to the contrary.

Additionally, it should be noted that in any given figure, some features may not be shown, or may be shown schematically, for clarity and/or simplicity. Additional details regarding some components and/or method steps may be illustrated in other figures in greater detail. The devices and/or methods disclosed herein may provide a number of desirable features and benefits as described in more detail below. For the purpose of this disclosure, the discussion below is directed toward a device and method for radially compressing a stent and will be so described in the interest of brevity. This, however, is not intended to be limiting as the skilled person will recognize that the following discussion may also apply to stent devices or medical implants including a stent with no or minimal changes to the structure and/or scope of the disclosure. Similarly, the devices and methods disclosed herein may have applications and uses for other medical devices.

Figure 1B:
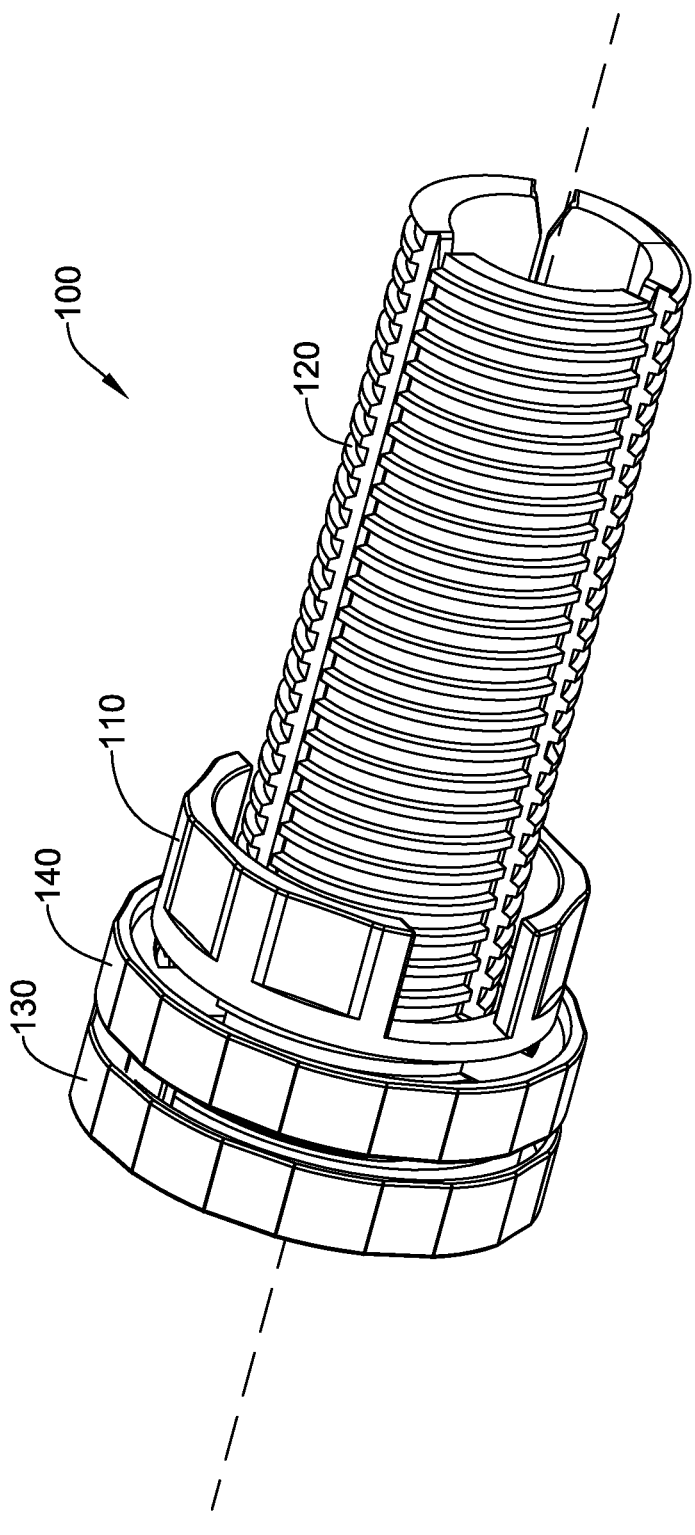
Figure 2:
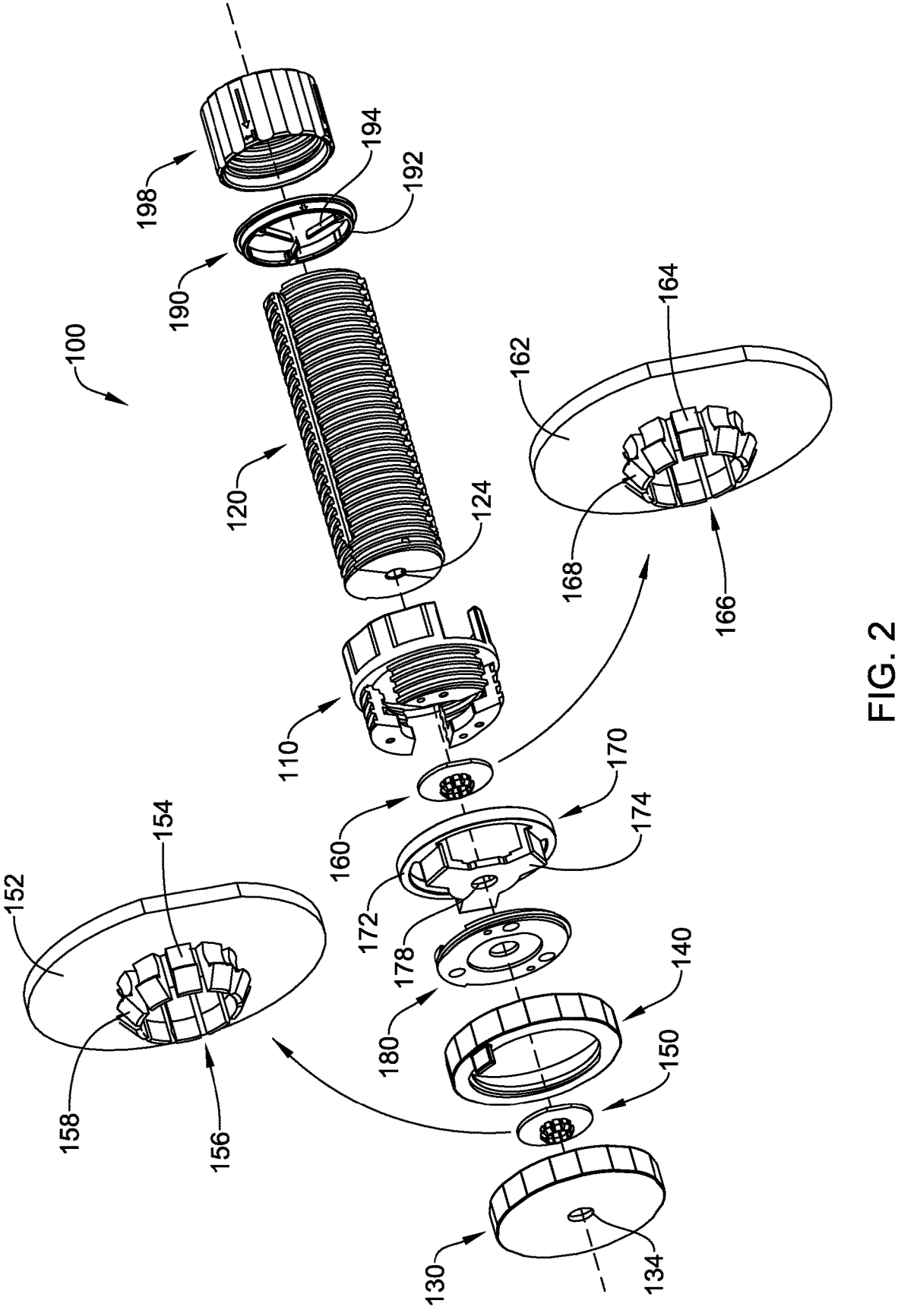
FIG. 2 is an exploded view illustrating selected aspects of the device of FIGS. 1A-1B.
Figure 3:
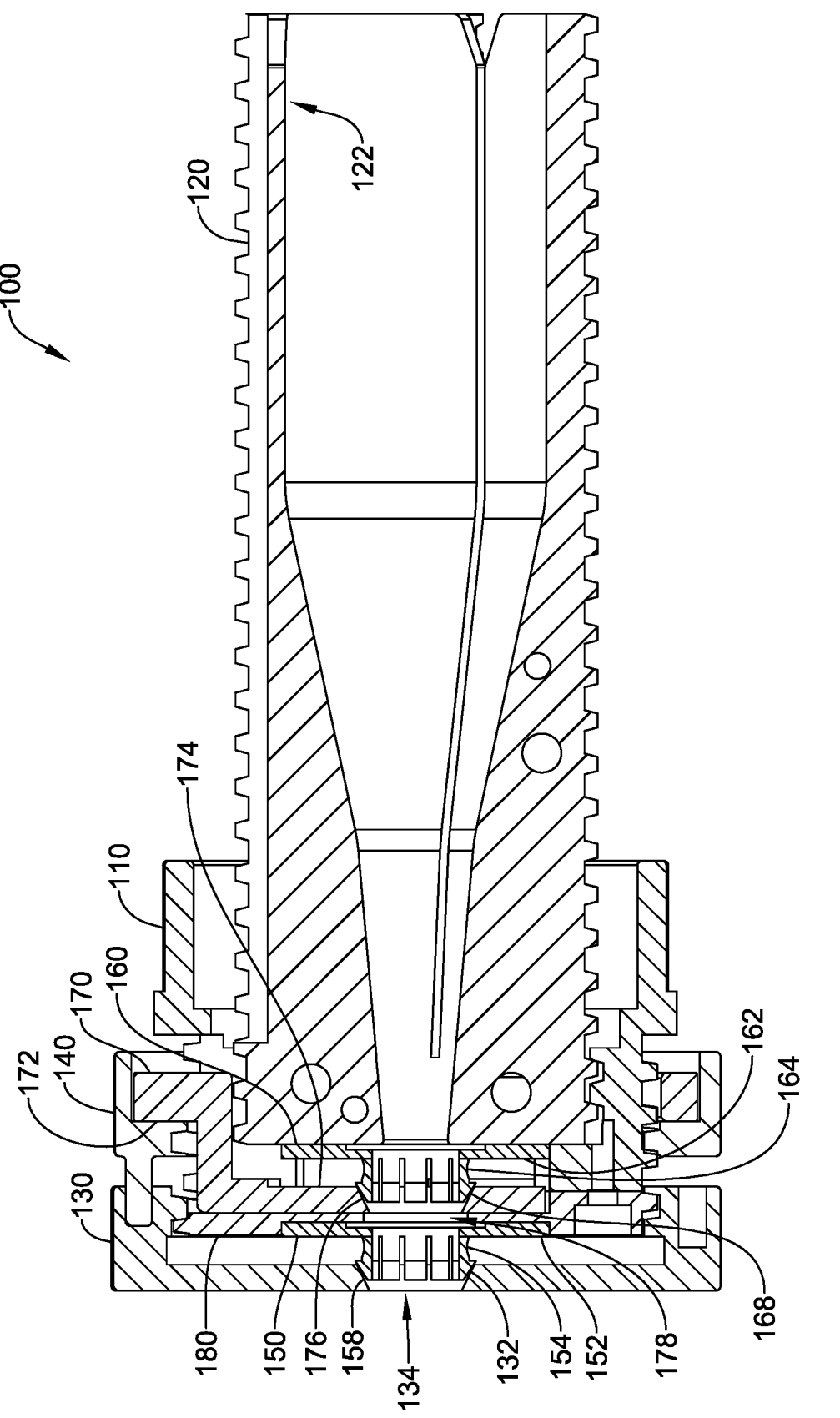
FIG. 3 is a partial cross-sectional view illustrating selected aspects of the device of FIGS. 1A-2.

FIGS. 1A-3 illustrate selected aspects of a device 100 for radially compressing a stent, wherein FIGS. 1A-1B illustrate different perspective views of the device 100, FIG. 2 illustrates an exploded view of the device 100, and FIG. 3 illustrates a partial cross-section of the device 100. As discussed herein, some elements of the device 100 may not be shown in every figure to improve clarity and/or understanding.

The device 100 may include a housing 110 extending along a central longitudinal axis and a loading funnel 120 removably coupled to the housing 110. In some embodiments, the device 100 may include a first threaded member 130 configured to engage the housing 110. In some embodiments, the device 100 may include a second threaded member 140 configured to engage the housing 110. Some suitable but non-limiting examples of materials that may be used to form the housing 110, the loading funnel 120, the first threaded member 130, and/or the second threaded member 140, including but not limited to metals and metal alloys, composites, ceramics, polymers, and the like, are described below. Additional details regarding one or more of these elements are provided herein.

In some embodiments, at least a portion of the housing 110 may include threads formed therein and/or thereon. In some embodiments, the housing 110 may include internal threads configured to threadably engage external threads formed on the loading funnel 120. In some embodiments, the housing 110 may include external threads configured to threadably engage the first threaded member 130 and/or the second threaded member 140. Other configurations are also contemplated.

In some embodiments, the loading funnel 120 may be removably coupled to the housing 110. In some embodiments, the loading funnel 120 may include external threads configured to engage internal threads formed in the housing 110. In some embodiments, the loading funnel 120 may be configured to rotatably engage with the housing 110 adjacent a first end of the loading funnel 120. Other configurations and/or means of engagement between the loading funnel 120 and the housing 110 are also contemplated. In some embodiments, the loading funnel 120 may be injection molded, cast, or machined. Other configurations and/or methods of production are also contemplated. In some embodiments, the loading funnel 120 may be formed as a monolithic structure from a single piece of material. In some embodiments, the loading funnel 120 may be formed from two or more individual pieces that are then assembled together using one or more known techniques.

In some embodiments, the loading funnel 120 may include an inner surface 122 having a taper. In some embodiments, the inner surface 122 of the loading funnel 120 may taper radially inward toward the first end of the loading funnel 120 and/or toward the housing 110. In some embodiments, the inner surface 122 of the loading funnel 120 may have its greatest inner extent at a second end opposite the first end of the loading funnel 120.

The device 100 may include a first iris 150 positioned adjacent the housing 110. In at least some embodiments, the first iris 150 may be positioned at least partially within the housing 110. The first iris 150 may include a first circumferential ring 152 extending and/or oriented transverse to the central longitudinal axis. In some embodiments, the first circumferential ring 152 may be generally disc-like in appearance. In some embodiments, the first iris 150 and/or the first circumferential ring 152 may have a substantially circular outer perimeter.

The first iris 150 may include a first plurality of arms 154 extending from the first circumferential ring 152 parallel to the central longitudinal axis. In some embodiments, the first plurality of arms 154 may be fixedly attached to the first circumferential ring 152. In some embodiments, the first plurality of arms 154 may be fixedly attached directly to the first circumferential ring 152. In some embodiments, the first plurality of arms 154 may extend from the first circumferential ring 152 in a first direction parallel to the central longitudinal axis. In some embodiments, the first direction may be toward the first threaded member 130 and/or away from the loading funnel 120. Other configurations are also contemplated.

In some embodiments, the first plurality of arms 154 of the first iris 150 may define a first central opening 156 positioned coaxially relative to the central longitudinal axis. In some embodiments, each of the first plurality of arms 154 of the first iris 150 may include a first tapered surface 158. In some embodiments, the first tapered surface 158 may taper radially inward as the first tapered surface 158 extends away from the first circumferential ring 152. In some embodiments, the first tapered surface 158 may taper radially inward in the first direction.

In some embodiments, the first iris 150 may include a first annular compression ring disposed within the first central opening 156 and/or engaged with the first plurality of arms 154. In some embodiments, the first annular compression ring may be formed from a polymeric material, such as silicone. In some embodiments, the first annular compression ring may be configured to engage an outer surface of a stent as the stent is compressed by the device 100.

In at least some embodiments, the first plurality of arms 154 may be integrally and/or monolithically formed with the first circumferential ring 152 from a single piece of material. Some suitable but non-limiting examples of materials that may be used to form the first iris 150, including but not limited to metals and metal alloys, composites, ceramics, polymers, and the like, are described below. In a preferred embodiment, the first iris 150 and/or the single piece of material is formed from a polymeric material. In at least some embodiments, the first plurality of arms 154 may be configured to resiliently flex, deflect, and/or bend to permit relative movement between adjacent arms of the first plurality of arms 154.

In some embodiments, the first iris 150 may be manufactured using one or more of a variety of methods. In some embodiments, the first iris 150 may be machined. In some embodiments, the first iris 150 may be cut using a waterjet. In some embodiments, the first iris 150 may be laser cut. In some embodiments, the first iris 150 may be injection molded. In some embodiments, the first iris 150 may be cast. Other methods of manufacture are also contemplated.

In some embodiments, the device 100 may include a second iris 160 positioned adjacent the housing 110. In at least some embodiments, the second iris 160 may be positioned at least partially within the housing 110. The second iris 160 may include a second circumferential ring 162 extending and/or oriented transverse to the central longitudinal axis. In some embodiments, the second circumferential ring 162 may be generally disc-like in appearance. In some embodiments, the second iris 160 and/or the second circumferential ring 162 may have a substantially circular outer perimeter. In some embodiments, the second iris 160 and/or the second circumferential ring 162 of the second iris 160 may be configured to engage and/or may abut the first end of the loading funnel 120 when the loading funnel 120 is engaged with the housing 110.

The second iris 160 may include a second plurality of arms 164 extending from the second circumferential ring 162 parallel to the central longitudinal axis. In some embodiments, the second plurality of arms 164 may be fixedly attached to the second circumferential ring 162. In some embodiments, the second plurality of arms 164 may be fixedly attached directly to the second circumferential ring 162. In some embodiments, the second plurality of arms 164 may extend from the second circumferential ring 162 in a second direction parallel to the central longitudinal axis. In some embodiments, the second direction may be toward the first threaded member 130 and/or away from the loading funnel 120. In some embodiments, the second direction may be, and/or may be the same as, the first direction. Other configurations are also contemplated.

In some embodiments, the second plurality of arms 164 of the second iris 160 may define a second central opening 166 positioned coaxially relative to the central longitudinal axis. In some embodiments, each of the second plurality of arms 164 of the second iris 160 may include a second tapered surface 168. In some embodiments, the second tapered surface 168 may taper radially inward as the second tapered surface 168 extends away from the second circumferential ring 162. In some embodiments, the second tapered surface 168 may taper radially inward in the second direction. Other configurations are also contemplated. In some embodiments, the second central opening 166 may be coaxial with and/or may be coaxially aligned with a first opening 124 formed in the first end of the loading funnel 120.

In some embodiments, the second iris 160 may include a second annular compression ring disposed within the second central opening 166 and/or engaged with the second plurality of arms 164. In some embodiments, the second annular compression ring may be formed from a polymeric material, such as silicone. In some embodiments, the second annular compression ring may be configured to engage the outer surface of the stent as the stent is compressed by the device 100.

In at least some embodiments, the second plurality of arms 164 may be integrally and/or monolithically formed with the second circumferential ring 162 from a single piece of material. Some suitable but non-limiting examples of materials that may be used to form the second iris 160, including but not limited to metals and metal alloys, composites, ceramics, polymers, and the like, are described below. In a preferred embodiment, the second iris 160 and/or the single piece of material is formed from a polymeric material. In at least some embodiments, the second iris 160 may be formed from the same material as the first iris 150. Other configurations are also contemplated. In at least some embodiments, the second plurality of arms 164 may be configured to resiliently flex, deflect, and/or bend to permit relative movement between adjacent arms of the second plurality of arms 164.

In some embodiments, the second iris 160 may be manufactured using one or more of a variety of methods. In some embodiments, the second iris 160 may be machined. In some embodiments, the second iris 160 may be cut using a waterjet. In some embodiments, the second iris 160 may be laser cut. In some embodiments, the second iris 160 may be injection molded. In some embodiments, the second iris 160 may be cast. Other methods of manufacture are also contemplated.

In some embodiments, the device 100 may include a compressor element 170 disposed between the second iris 160 and the second threaded member 140. In some embodiments, the compressor element 170 may be disposed between the second iris 160 and the housing 110. In some embodiments, a first portion 172 of the compressor element 170 may be disposed radially outward of the housing 110. In some embodiments, a second portion 174 of the compressor element 170 may be disposed radially inward of the housing 110. The compressor element 170 may be movable relative to the housing 110. In some embodiments, the compressor element 170 may be axially movable relative to the housing 110. Some suitable but non-limiting examples of materials that may be used to form the compressor element 170, including but not limited to metals and metal alloys, composites, ceramics, polymers, and the like, are described below.

In some embodiments, the compressor element 170 may be manufactured using one or more of a variety of methods. In some embodiments, the compressor element 170 may be machined. In some embodiments, the compressor element 170 may be cut using a waterjet. In some embodiments, the compressor element 170 may be laser cut. In some embodiments, the compressor element 170 may be injection molded. In some embodiments, the compressor element 170 may be cast. Other methods of manufacture are also contemplated.

In some embodiments, the device 100 may include a cover plate 180 positioned adjacent the housing 110. In some embodiments, the cover plate 180 may be releasably secured to the housing 110. In some embodiments, the cover plate 180 may be releasably secured to the housing 110 over the compressor element 170. In some embodiments, the cover plate 180 may releasably secure the compressor element 170 to and/or at least partially within the housing 110. In at least some embodiments, the cover plate 180 may be releasably secured to the housing 110 using mechanical fasteners. In some embodiments, the cover plate 180 may be releasably secured to the housing 110 using a threaded engagement, a tab and slot system, or other suitable means of securement. Other configurations and/or combinations thereof are also contemplated. In some embodiments, the cover plate 180 may be configured to secure the compressor element 170 to the housing 110 such that the first portion 172 of the compressor element 170 is disposed radially outward of the housing 110 and the second portion 174 of the compressor element 170 is disposed radially inward of the housing 110. Some suitable but non-limiting examples of materials that may be used to form the cover plate 180, including but not limited to metals and metal alloys, composites, ceramics, polymers, and the like, are described below.

In some embodiments, the second iris 160 may be axially offset from the first iris 150. In some embodiments, the second iris 160 may be axially spaced apart from the first iris 150. In some embodiments, the cover plate 180 may be disposed between the second iris 160 and the first iris 150. In some embodiments, the first iris 150 and/or the first circumferential ring 152 of the first iris 150 may engage and/or abut the cover plate 180. Alternatively, in some embodiments, the second iris 160 may be disposed adjacent to the first iris 150. In some embodiments, the second iris 160 may be configured to engage the first iris 150. In some embodiments, the second iris 160 may abut the first iris 150. In some embodiments, the second circumferential ring 162 of the second iris 160 may abut the first circumferential ring 152 of the first iris 150. Other configurations are also contemplated.

In some embodiments, the device may include a star pusher 190 (e.g., FIG. 2) configured to translate axially along the loading funnel 120 and a star pusher nut 198 (e.g., FIG. 2) configured to engage the loading funnel 120. The star pusher nut 198 may be configured to rotatably and/or threadably engage the loading funnel 120. In some embodiments, the loading funnel 120 may include external threads configured to receive internal threads formed in the star pusher nut 198. The star pusher nut 198 may be configured to rotate relative to the loading funnel 120. The star pusher nut 198 may be configured to translate axially relative to the loading funnel 120. In at least some embodiments, rotation of the star pusher nut 198 relative to the loading funnel 120 when the star pusher nut 198 is engaged with the loading funnel 120 may translate the star pusher nut 198 axially along and/or relative to the loading funnel 120. Some suitable but non-limiting examples of materials that may be used to form the star pusher 190 and/or the star pusher nut 198, including but not limited to metals and metal alloys, composites, ceramics, polymers, and the like, are described below.

In some embodiments, the star pusher nut 198 may be configured to engage the star pusher 190. In some embodiments, the star pusher nut 198 may be configured to translate the star pusher 190 along and/or relative to the loading funnel 120. In some embodiments, the star pusher nut 198 may be configured to translate the star pusher 190 axially along and/or relative to the loading funnel 120. In some embodiments, the star pusher nut 198 may be configured to translate the star pusher 190 along and/or relative to the loading funnel 120 as the star pusher nut 198 is rotated relative to the loading funnel 120. In some embodiments, the star pusher nut 198 may be configured to translate the star pusher 190 axially along and/or relative to the loading funnel 120 as the star pusher nut 198 is rotated relative to the loading funnel 120.

The star pusher 190 may include an outer ring 192 and a plurality of legs 194 extending radially inward from the outer ring 192. The plurality of legs 194 may be configured to be disposed in and/or to project through a plurality of longitudinal slots formed through a side wall of the loading funnel 120. As such, the star pusher 190 may be non-rotatable relative to the loading funnel 120 when the star pusher 190 is engaged with the loading funnel 120. The star pusher 190 may be adapted and/or configured to push and/or translate a stent axially along, relative to, and/or through the loading funnel 120 as the star pusher 190 is translated axially along and/or relative to the loading funnel 120. In at least some embodiments, the stent may be a component of and/or may be included in a medical implant. In some embodiments, the medical implant may include and/or may be a replacement heart valve implant.

The first threaded member 130 may be configured to rotatably and/or threadably engage the housing 110. In some embodiments, the first threaded member 130 may be configured to engage the first plurality of arms 154 of the first iris 150. In some embodiments, rotation of the first threaded member 130 relative to the housing 110 may change a size of the first central opening 156 of the first iris 150. In some embodiments, the first plurality of arms 154 of the first iris 150 may be configured to deflect radially between a first configuration and a second configuration upon rotation of the first threaded member 130 relative to the housing 110. In at least some embodiments, the first plurality of arms 154 of the first iris 150 may be self-biased toward the first configuration. In some embodiments, the first central opening 156 of the first iris 150 may have a first size in the first configuration and a second size in the second configuration less than the first size.

In some embodiments, the first threaded member 130 may include a first angled surface 132 (e.g., FIG. 3) defining a first central aperture 134 of the first threaded member 130. In some embodiments, the first tapered surface 158 of the first plurality of arms 154 of the first iris 150 may be configured to engage the first angled surface 132 of the first threaded member 130 as the first threaded member 130 is rotated relative to the housing 110.

In some embodiments, the first plurality of arms 154 of the first iris 150 may be configured to deflect radially inward from the first configuration toward the second configuration upon rotation of the first threaded member 130 relative to the housing 110. In some embodiments, the first plurality of arms 154 of the first iris 150 may be configured to deflect radially inward from the first configuration toward the second configuration upon clockwise rotation of the first threaded member 130 relative to the housing 110. Other configurations are also contemplated.

In some embodiments, the first plurality of arms 154 of the first iris 150 may be configured to deflect radially outward from the second configuration toward the first configuration upon rotation of the first threaded member 130 relative to the housing 110. In some embodiments, the first plurality of arms 154 of the first iris 150 may be configured to deflect radially outward from the second configuration toward the first configuration upon counterclockwise rotation of the first threaded member 130 relative to the housing 110. Other configurations are also contemplated.

The second threaded member 140 may be configured to rotatably and/or threadably engage the housing 110. In some embodiments, the second threaded member 140 may be configured to engage the compressor element 170 and the compressor element 170 may be configured to engage the second plurality of arms 164 of the second iris 160. In some embodiments, the second threaded member 140 may be configured to engage the first portion 172 of the compressor element 170 and the compressor element 170 may be configured to engage the second plurality of arms 164 of the second iris 160 as the second threaded member 140 is rotated relative to the housing 110. In some embodiments, the compressor element 170 may be axially translated relative to the housing 110 via rotation of the second threaded member 140 relative to the housing 110.

In some embodiments, rotation of the second threaded member 140 relative to the housing 110 may change a size of the second central opening 166 of the second iris 160.

In some embodiments, the second plurality of arms 164 of the second iris 160 may be configured to deflect radially between a first configuration and a second configuration upon rotation of the second threaded member 140 relative to the housing 110. In at least some embodiments, the second plurality of arms 164 of the second iris 160 may be self-biased toward the first configuration. In some embodiments, the second central opening 166 of the second iris 160 may have a first size in the first configuration and a second size in the second configuration less than the first size.

In some embodiments, the compressor element 170 may include a second angled surface 176 (e.g., FIG. 3) defining a second central aperture 178 of the compressor element 170. In some embodiments, the second tapered surface 168 of the second plurality of arms 164 of the second iris 160 may be configured to engage the second angled surface 176 of the compressor element 170 as the second threaded member 140 is rotated relative to the housing 110.

In some embodiments, the second plurality of arms 164 of the second iris 160 may be configured to deflect radially inward from the first configuration toward the second configuration upon rotation of the second threaded member 140 relative to the housing 110. In some embodiments, the second plurality of arms 164 of the second iris 160 may be configured to deflect radially inward from the first configuration toward the second configuration upon clockwise rotation of the second threaded member 140 relative to the housing 110. Other configurations are also contemplated.

In some embodiments, the second plurality of arms 164 of the second iris 160 may be configured to deflect radially outward from the second configuration toward the first configuration upon rotation of the second threaded member 140 relative to the housing 110. In some embodiments, the second plurality of arms 164 of the second iris 160 may be configured to deflect radially outward from the second configuration toward the first configuration upon counterclockwise rotation of the second threaded member 140 relative to the housing 110. Other configurations are also contemplated.

In some embodiments, the first threaded member 130 and the second threaded member 140 may be configured to rotate relative to the housing 110 independently of each other. In some embodiments, the first threaded member 130 may be movable relative to the housing 110 independently of the second threaded member 140. In some embodiments, the second threaded member 140 may be movable relative to the housing 110 independently of the first threaded member 130.

In some embodiments, the first threaded member 130 and the second threaded member 140 may be movable relative to the housing 110 together, in tandem, and/or simultaneously. In some embodiments, the first threaded member 130 and the second threaded member 140 may be movable relative to the housing 110 together, in tandem, and/or simultaneously at one time, in one direction, or during a particular step of a method disclosed herein, and the first threaded member 130 and the second threaded member 140 may be movable relative to the housing 110 independently of each other at another time, in another direction, or during another particular step of a method disclosed herein. Other configurations are also contemplated.

FIGS. 4-7 are cross-sectional views of the device 100 showing selected aspects of a method of radially compressing a stent 200. The device 100 may generally include elements and/or features as described herein. For improved clarity and understanding, some elements or features of the device 100 and/or the stent 200 are not shown or are not shown in their entirety. In some instances, reference numbers discussed in the context of FIGS. 4-7 may not be shown, and the reader may refer back to FIGS. 2-3.

The stent 200 include an expandable framework defining a central lumen which, in some embodiments, may be substantially cylindrical. In some embodiments, the expandable framework may have a substantially circular cross-section. In some embodiments, the expandable framework can have a non-circular (e.g., D-shaped, elliptical, etc.) cross-section. In some embodiments, a non-circular expandable framework can be used to repair a mitral valve or another non-circular valve in the patient's heart or body. Some suitable but non-limiting examples of materials that may be used to form the expandable framework, including but not limited to metals and metal alloys, composites, ceramics, polymers, and the like, are described below.

The stent 200 and/or the expandable framework may be configured to shift from a collapsed configuration to an expanded configuration. In some embodiments, the expandable framework may be self-expanding. In some embodiments, the expandable framework may be self-biased toward the expanded configuration. In some embodiments, the expandable framework may be mechanically expandable. In some embodiments, the expandable framework may be balloon expandable. Other configurations are also contemplated.

In some embodiments, the stent 200 may be a part of a replacement heart valve implant. It will be appreciated that the replacement heart valve implant can be any type of heart valve (e.g., a mitral valve, an aortic valve, etc.). The replacement heart valve implant can be configured to allow one-way flow through the replacement heart valve implant from an inflow end to an outflow end. In some embodiments of a replacement heart valve implant, the stent 200 and/or the expandable framework may define a lower crown proximate an inflow end of the replacement heart valve implant, an upper crown proximate an outflow end of the replacement heart valve implant, and a plurality of stabilization arches extending downstream from the outflow end.

In some embodiments, the replacement heart valve implant may include a plurality of valve leaflets disposed within the central lumen. The plurality of valve leaflets may be coupled, secured, and/or fixedly attached to the stent 200 and/or the expandable framework. In some embodiments, the plurality of valve leaflets can be integrally formed with each other, such that the plurality of valve leaflets is formed as a single unitary and/or monolithic unit. In some embodiments, the plurality of valve leaflets may be formed integrally with other structures such as an inner skirt and/or an outer skirt, base structures, liners, or the like. The plurality of valve leaflets may be configured to substantially restrict fluid from flowing through the replacement heart valve implant in a closed position. For example, in some embodiments, free edges of the plurality of valve leaflets may move into coaptation with one another in the closed position to substantially restrict fluid from flowing through the replacement heart valve implant. The free edges of the plurality of valve leaflets may be move apart from each other in an open position to permit fluid flow through the replacement heart valve implant.

In some embodiments, the replacement heart valve implant may include an inner skirt. The inner skirt may be disposed on and/or extend along an inner surface of the stent 200 and/or the expandable framework. In at least some embodiments, the inner skirt may be fixedly attached to the stent 200 and/or the expandable framework. The inner skirt may direct fluid, such as blood, flowing through the replacement heart valve implant toward the plurality of valve leaflets. In at least some embodiments, the inner skirt may be fixedly attached to and/or integrally formed with the plurality of valve leaflets. The inner skirt may ensure the fluid flows through the central lumen and does not flow around the plurality of valve leaflets when they are in the closed position.

In some embodiments, the replacement heart valve implant may include an outer skirt. In some embodiments, the outer skirt may be disposed on and/or extend along an outer surface of the stent 200 and/or the expandable framework. In some embodiments, the outer skirt may be disposed between the stent 200 and/or the expandable framework and native tissue in order to prevent fluid, such as blood, flowing around the stent 200 and/or the expandable framework in a downstream direction so as to ensure that the plurality of valve leaflets can stop the flow of fluid when in the closed position.

In some embodiments, the plurality of valve leaflets may be comprised of a polymer, such as a thermoplastic polymer. In some embodiments, the plurality of valve leaflets may include at least 50 percent by weight of a polymer. In some embodiments, the plurality of valve leaflets may be formed from bovine pericardial or other living tissue. Other configurations and/or materials are also contemplated.

In some embodiments, the inner skirt and/or the outer skirt may include a polymer, such as a thermoplastic polymer. In some embodiments, the inner skirt and/or the outer skirt may include at least 50 percent by weight of a polymer. In some embodiments one or more of the plurality of valve leaflets, the inner skirt, and/or the outer skirt may be formed of the same polymer or polymers. In some embodiments, the polymer may be a polyurethane. In some embodiments, the inner skirt and/or the outer skirt may be substantially impervious to fluid. In some embodiments, the inner skirt and/or the outer skirt may be formed from a thin tissue (e.g., bovine pericardial, etc.). In some embodiments, the inner skirt and/or the outer skirt may be formed from a coated fabric material. In some embodiments, the inner skirt and/or the outer skirt may be formed from a nonporous and/or impermeable fabric material. Other configurations are also contemplated. Some suitable but non-limiting examples of materials that may be used to form the inner skirt and/or the outer skirt including but not limited to polymers, composites, and the like, are described below.

In some embodiments, the stent 200 and/or the replacement heart valve implant may have an outer extent of about 23 millimeters (mm), about 25 mm, about 27 mm, about 30 mm, etc. in an unconstrained configuration (e.g., in the expanded configuration). In some embodiments, the stent 200 and/or the replacement heart valve implant may have an outer extent of about 10 mm, about 9 mm about 8 mm, about 7 mm, about 6 mm, etc. in the collapsed configuration. Other configurations are also contemplated.

Figure 4:
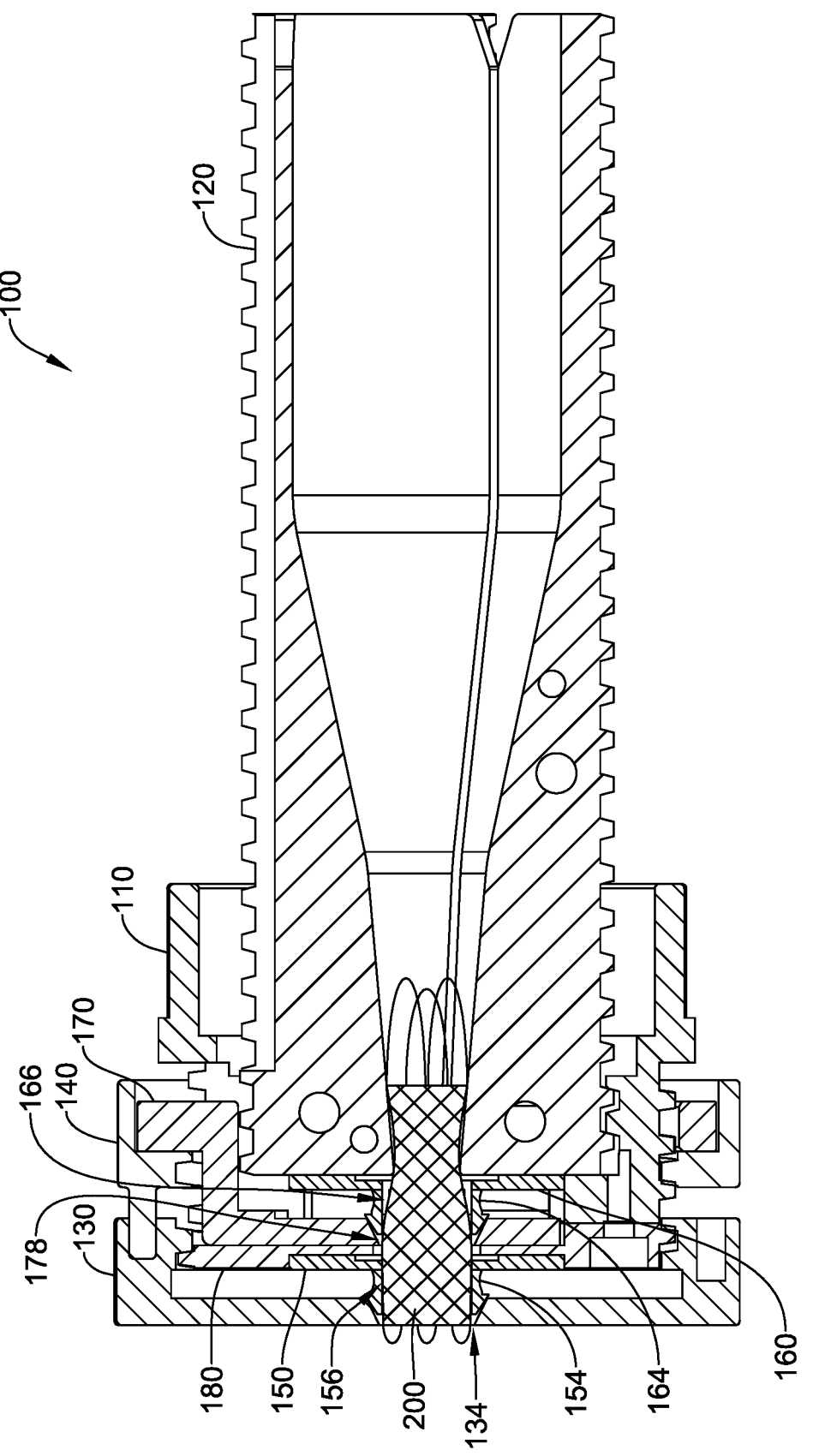
FIGS. 4-7 are partial cross-sectional views illustrating selected aspects of a method of radially compressing a stent using the device of FIGS. 1A-3.

A method of radially compressing a stent may include inserting a stent 200 in a first configuration through the loading funnel 120 removably coupled to the housing 110 into the first central opening 156 of the first iris 150, as seen in FIG. 4. In some embodiments, in the first configuration, the stent 200 may be in an expanded configuration. In some embodiments, in the first configuration, the stent 200 may be in a partially collapsed state. For example, in some embodiments, the device 100 may include the loading funnel 120 adapted to partially collapse the stent 200 as the stent 200 is inserted into the first central opening 156 of the first iris 150. In some embodiments, the loading funnel 120 may be configured to releasably attach to the housing 110, as described herein. For example, in the view shown in FIG. 4, the loading funnel 120 may be configured to be inserted into the housing 110 from the right side of the view until at least a portion of the loading funnel 120 is positioned adjacent to and/or is engaged with the housing 110. In some embodiments, the method may include inserting the stent 200 into and/or through the loading funnel 120 before inserting the stent 200 in the first configuration into the first central opening 156 of the first iris 150.

In some embodiments, inserting the stent 200 may include advancing the stent 200 through the loading funnel 120 using the star pusher 190 and the star pusher nut 198. In some embodiments, as the star pusher nut 198 is rotated relative to the loading funnel 120, the star pusher nut 198 translates axially along the loading funnel 120. As the star pusher nut 198 translates along the loading funnel 120, the star pusher 190 is similarly translated along the loading funnel 120 to push the stent 200 axially within and/or through the loading funnel 120.

In some embodiments, the method may include inserting the stent 200 in the first configuration into the second central opening 166 of the second iris 160 axially offset from the first iris 150. In some embodiments, the method may include inserting the stent 200 through the second central aperture 178 of the compressor element 170 and/or the cover plate 180. In some embodiments, the method may include inserting the stent 200 through the second central aperture 178 of the compressor element 170 and/or the cover plate 180 before inserting the stent 200 into the first central opening 156 of the first iris 150. Other configurations are also contemplated.

Figure 5:
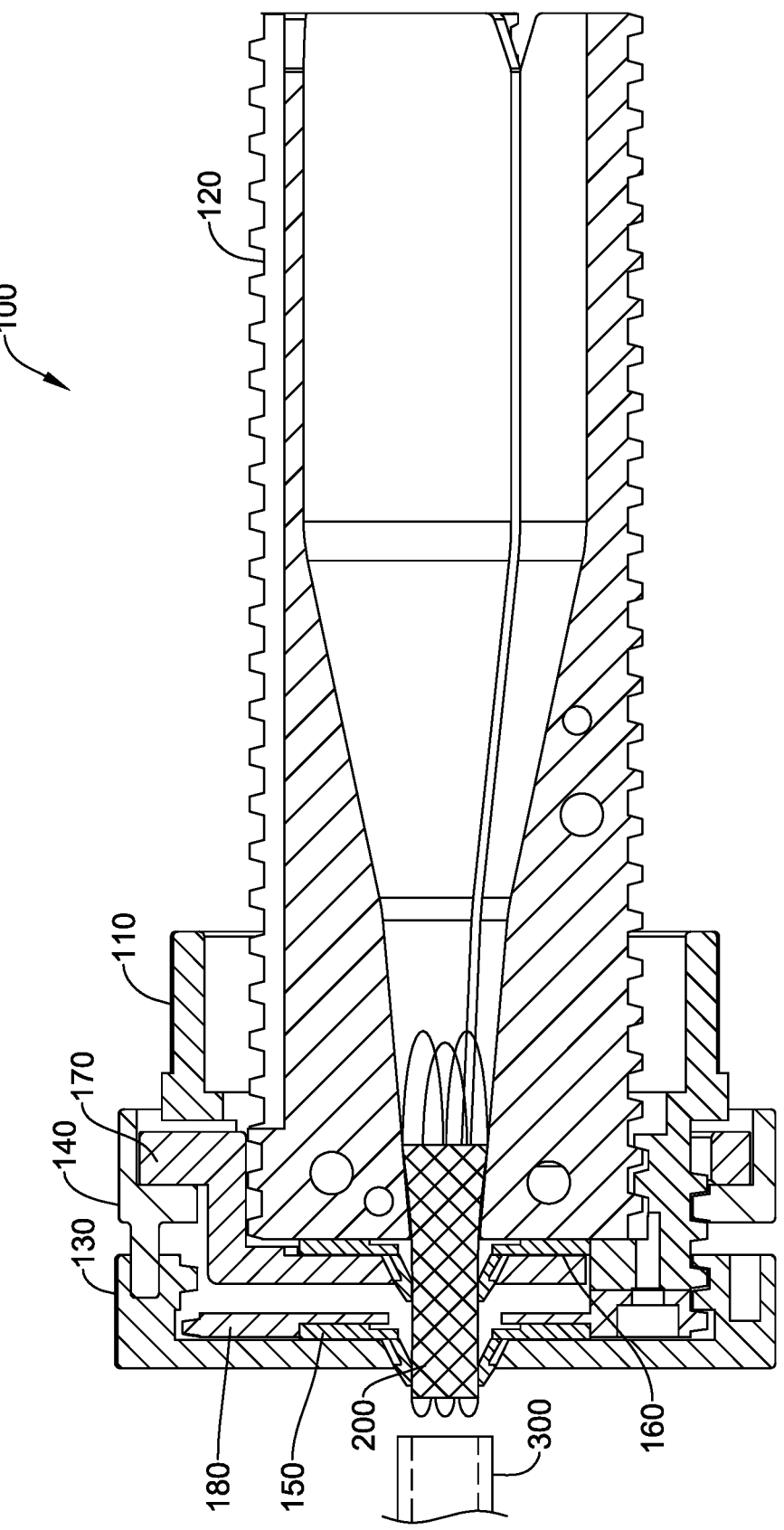

The method may include rotating the first threaded member 130 relative to the housing 110 and/or the first iris 150 to shift the first plurality of arms 154 of the first iris 150 from the first configuration toward and/or to the second configuration, as seen in FIG. 5, wherein the first central opening 156 has a first size in the first configuration (e.g., FIG. 4) and a second size in the second configuration less than the first size (e.g., FIG. 5). In some embodiments, the method may include rotating the first threaded member 130 clockwise relative to the housing 110 to shift the first plurality of arms 154 of the first iris 150 from the first configuration toward and/or to the second configuration. In the second configuration of the first plurality of arms 154 of the first iris 150, a first portion of the stent 200 disposed within the first iris 150 and/or the first central opening 156 of the first iris 150 may be in a radially compressed configuration.

In some embodiments, the method may include rotating the second threaded member 140 relative to the housing 110 to shift the second plurality of arms 164 of the second iris 160 from a first configuration toward and/or to a second configuration, wherein the second central opening 166 has a first size in the first configuration (e.g., FIG. 4) and a second size in the second configuration (e.g., FIG. 5) less than the first size. In some embodiments, the method may include rotating the second threaded member 140 clockwise relative to the housing 110 to shift the second plurality of arms 164 of the second iris 160 from the first configuration toward and/or to the second configuration. In the second configuration of the second plurality of arms 164 of the second iris 160, a second portion of the stent 200 disposed within the second iris 160 and/or the second central opening 166 of the second iris 160 may be in the radially compressed configuration.

Figure 6:
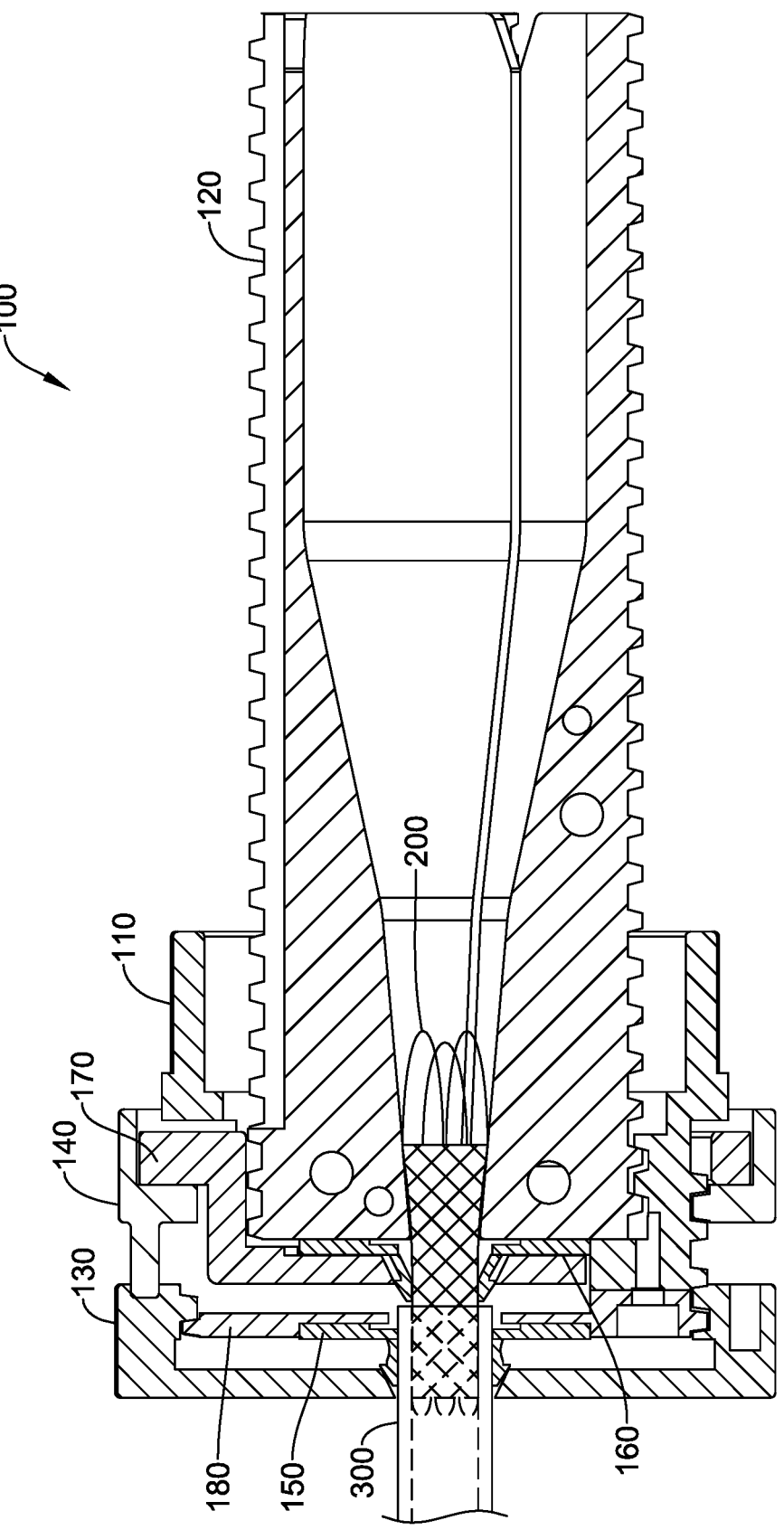

In some embodiments, the method may include positioning a sheath 300 proximate the first iris 150 with the first plurality of arms 154 in the second configuration and the first portion of the stent 200 disposed within the first iris 150 and/or the first central opening 156 in the radially compressed configuration, as seen in FIG. 5. After positioning the sheath 300 proximate the first iris 150, the method may include rotating the first threaded member 130 relative to the housing 110 to shift the first plurality of arms 154 from the second configuration toward and/or to the first configuration. In some embodiments, the method may include rotating the first threaded member 130 counterclockwise relative to the housing 110 to shift the first plurality of arms 154 from the second configuration to the first configuration. The method may further include moving the sheath 300 into the first iris 150 over the stent 200 in the compressed configuration such that the first portion of the stent 200 that was disposed within the first iris 150 is disposed within a lumen of the sheath 300, as seen in FIG. 6. In some embodiments, the sheath 300 has an inner diameter less than an outer diameter of the stent 200 in the first configuration. As such, radial compression of the stent 200 is required in order to move the stent 200 into the lumen of the sheath 300.

Figure 7:
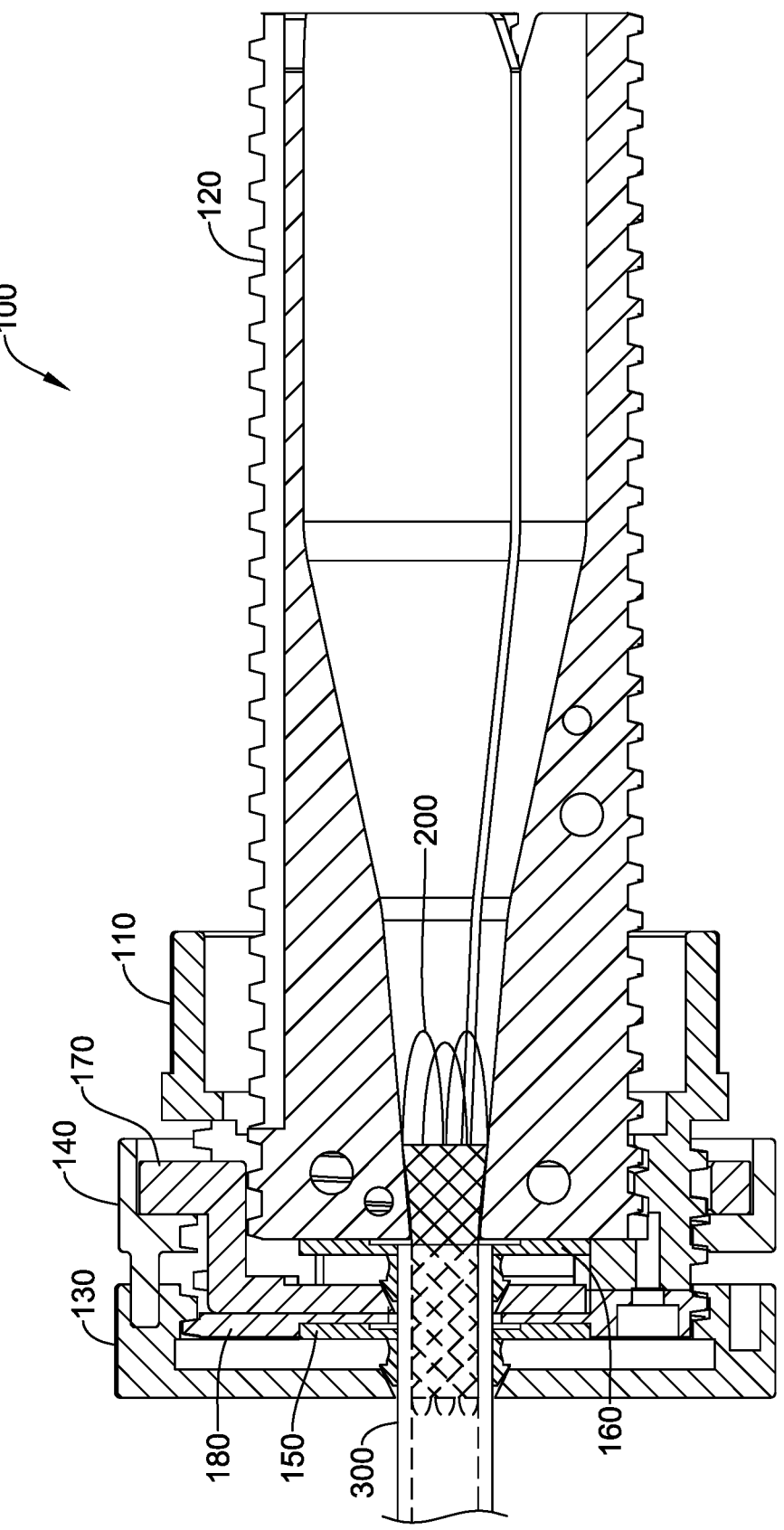

In some embodiments, after moving the sheath 300 into the first iris 150 over the stent 200, the method may further include rotating the second threaded member 140 relative to the housing 110 to shift the second plurality of arms 164 of the second iris 160 from the second configuration toward and/or to the first configuration. In some embodiments, the method may include rotating the second threaded member 140 counterclockwise relative to the housing 110 to shift the second plurality of arms 164 of the second iris 160 from the second configuration toward and/or to the first configuration. The method may further include moving the sheath 300 into the second iris 160 over the stent 200 in the compressed configuration such that the second portion of the stent 200 that was disposed within the second iris 160 is disposed within the lumen of the sheath 300, as seen in FIG. 7.

In some embodiments, the device 100 may permit the stent 200 to be loaded into the sheath 300 without moving or advancing the stent 200 through the device 100 multiple times, thereby reducing the number of steps required to sheath the stent 200, reducing or eliminating multiple compression steps, and/or reducing opportunity for damage to the stent 200. In some embodiments, the device 100 may be reusable following suitable sterilization techniques. In some embodiments, the device 100 may be disposable and/or may be classified or used as a single-use device.

Additionally, it is contemplated that the device 100 may include additional irises, etc. to accommodate a stent of longer length and/or varying outer diameter (in a first configuration and/or in a compressed configuration). For example, in some embodiments, the second size of the first central opening 156 of the first iris 150 may be the same as the second size of the second central opening 166 of the second iris 160, and additional central openings of additional irises may have a second size that is the same as the second size of the first central opening 156 and/or the second central opening 166. In some embodiments, the second size of the first central opening 156 of the first iris 150 may be different from the second size of the second central opening 166 of the second iris 160, and additional central openings of additional irises may have a second size that is the same as the second size of the first central opening 156 and the second central opening 166, the additional central openings of additional irises may have a second size that is the same as the second size of one of the first central opening 156 and the second central opening 166, or the additional central openings of additional irises may have a second size that is the different from the second size of the first central opening 156 and the second central opening 166. Other configurations are also contemplated.

In some embodiments, wherein the device 100 includes additional irises, the process described above with respect to moving the sheath 300 into the first iris 150 and the second iris 160 may be repeated as necessary to move the sheath 300 over additional portions of the stent 200 disposed within those irises.

Additionally, in some embodiments, if additional length of the stent 200 needs to be moved into the sheath 300, the stent 200 may be advanced through the loading funnel 120 into the first iris 150 and the second iris 160, and the first iris 150 and the second iris 160 may be again shifted from the first configuration to the second configuration and the process may be repeated.

In some embodiments, after moving the sheath 300 into the second iris 160 over the stent 200 such that the second portion of the stent 200 that was disposed within the second iris 160 is disposed within the lumen of the sheath 300, the sheath 300 and the first and second portions of the stent 200 that were disposed within the first and second irises, respectively, may be advanced through the housing 110 and/or the loading funnel 120, and a separate sheath may be translated over an uncovered portion of the stent 200 toward the sheath 300 to cover at least some of the uncovered portion of the stent 200 that remains outside of the sheath 300. Other configurations are also contemplated.

Figure 8:
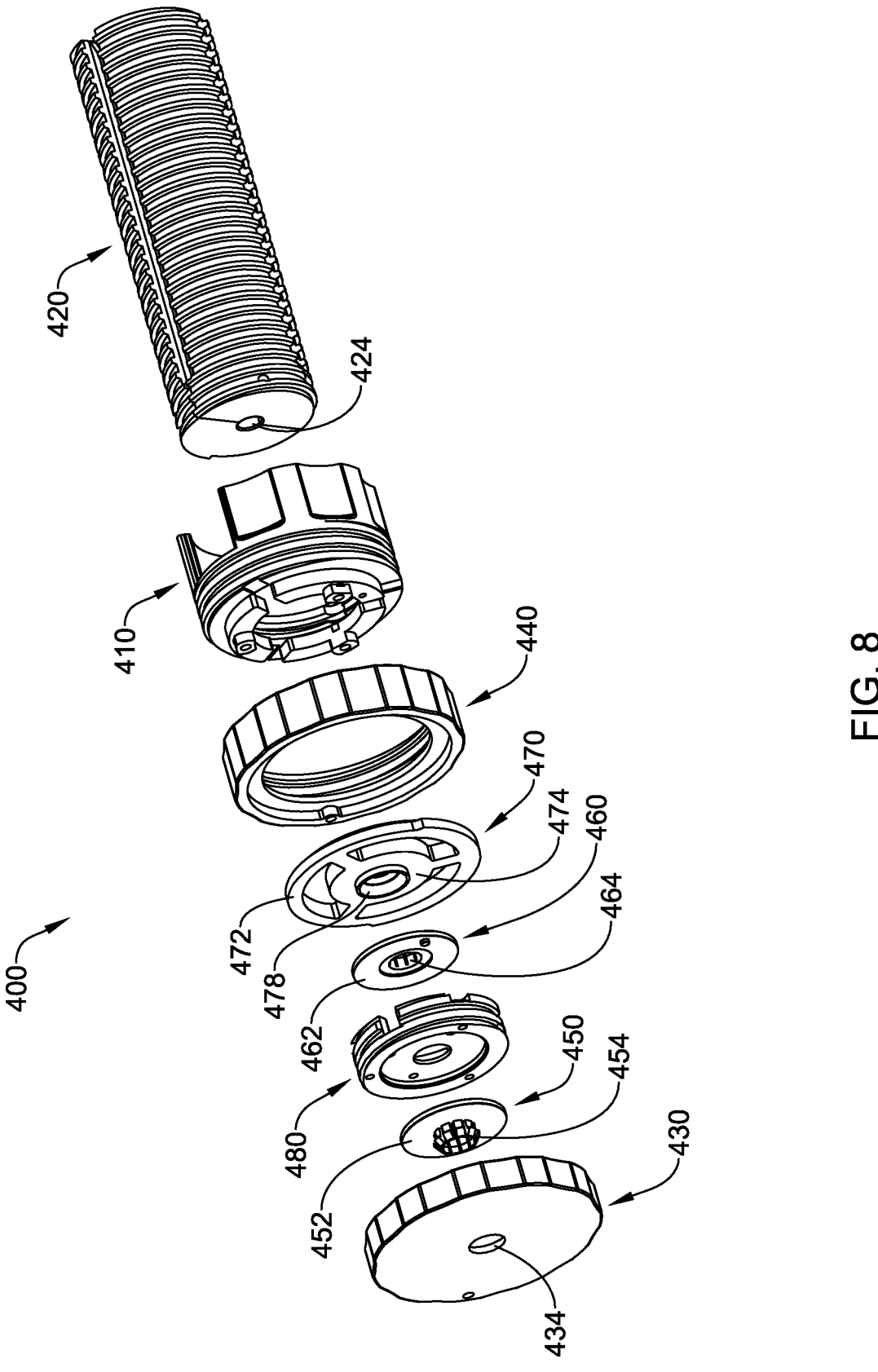
FIG. 8 is an exploded view illustrating selected aspects of an alternative configuration of a device for radially compressing a stent.
Figure 9:
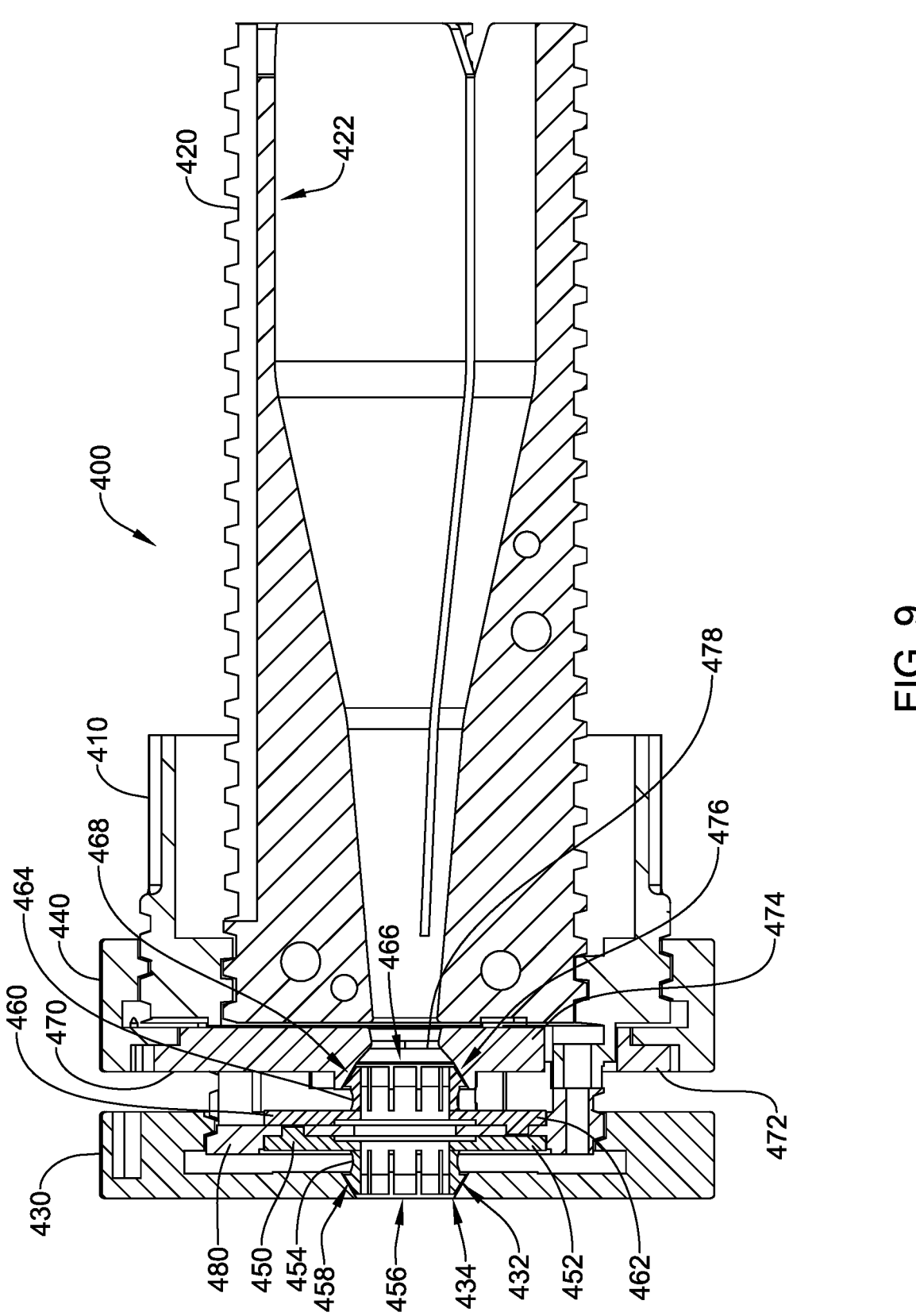
FIG. 9 is a partial cross-sectional view illustrating selected aspects of the device of FIG. 8.

FIGS. 8-9 illustrate selected aspects of an alternative configuration of a device 400 for radially compressing a stent, wherein FIG. 8 illustrates an exploded view of the device 400 and FIG. 9 illustrates a partial cross-section of the device 400. As discussed herein, some elements of the device 400 may not be shown in every figure to improve clarity and/or understanding.

The device 400 may include a housing 410 extending along a central longitudinal axis and a loading funnel 420 removably coupled to the housing 410. In some embodiments, the device 400 may include a first threaded member 430 configured to engage the housing 410. In some embodiments, the device 400 may include a second threaded member 440 configured to engage the housing 410. Some suitable but non-limiting examples of materials that may be used to form the housing 410, the loading funnel 420, the first threaded member 430, and/or the second threaded member 440, including but not limited to metals and metal alloys, composites, ceramics, polymers, and the like, are described below. Additional details regarding one or more of these elements are provided herein.

In some embodiments, at least a portion of the housing 410 may include threads formed therein and/or thereon. In some embodiments, the housing 410 may include internal threads configured to threadably engage external threads formed on the loading funnel 420. In some embodiments, the housing 410 may include external threads configured to threadably engage the first threaded member 430 and/or the second threaded member 440. Other configurations are also contemplated.

In some embodiments, the loading funnel 420 may be removably coupled to the housing 410. In some embodiments, the loading funnel 420 may include external threads configured to engage internal threads formed in the housing 410. In some embodiments, the loading funnel 420 may be configured to rotatably engage with the housing 410 adjacent a first end of the loading funnel 420. Other configurations and/or means of engagement between the loading funnel 420 and the housing 410 are also contemplated. In some embodiments, the loading funnel 420 may be injection molded, cast, or machined. Other configurations and/or methods of production are also contemplated. In some embodiments, the loading funnel 420 may be formed as a monolithic structure from a single piece of material. In some embodiments, the loading funnel 420 may be formed from two or more individual pieces that are then assembled together using one or more known techniques.

In some embodiments, the loading funnel 420 may include an inner surface 422 having a taper. In some embodiments, the inner surface 422 of the loading funnel 420 may taper radially inward toward the first end of the loading funnel 420 and/or toward the housing 410. In some embodiments, the inner surface 422 of the loading funnel 420 may have its greatest inner extent at a second end opposite the first end of the loading funnel 420.

The device 400 may include a first iris 450 positioned adjacent the housing 410. In at least some embodiments, the first iris 450 may be positioned at least partially within the housing 410. The first iris 450 may include a first circumferential ring 452 extending and/or oriented transverse to the central longitudinal axis. In some embodiments, the first circumferential ring 452 may be generally disc-like in appearance. In some embodiments, the first iris 450 and/or the first circumferential ring 452 may have a substantially circular outer perimeter.

The first iris 450 may include a first plurality of arms 454 extending from the first circumferential ring 452 parallel to the central longitudinal axis. In some embodiments, the first plurality of arms 454 may be fixedly attached to the first circumferential ring 452. In some embodiments, the first plurality of arms 454 may be fixedly attached directly to the first circumferential ring 452. In some embodiments, the first plurality of arms 454 may extend from the first circumferential ring 452 in a first direction parallel to the central longitudinal axis. In some embodiments, the first direction may be toward the first threaded member 430 and/or away from the loading funnel 420. Other configurations are also contemplated.

In some embodiments, the first plurality of arms 454 of the first iris 450 may define a first central opening 456 positioned coaxially relative to the central longitudinal axis. In some embodiments, each of the first plurality of arms 454 of the first iris 450 may include a first tapered surface 458. In some embodiments, the first tapered surface 458 may taper radially inward as the first tapered surface 458 extends away from the first circumferential ring 452. In some embodiments, the first tapered surface 458 may taper radially inward in the first direction.

In at least some embodiments, the first plurality of arms 454 may be integrally and/or monolithically formed with the first circumferential ring 452 from a single piece of material. Some suitable but non-limiting examples of materials that may be used to form the first iris 450, including but not limited to metals and metal alloys, composites, ceramics, polymers, and the like, are described below. In a preferred embodiment, the first iris 450 and/or the single piece of material is formed from a polymeric material. In at least some embodiments, the first plurality of arms 454 may be configured to resiliently flex, deflect, and/or bend to permit relative movement between adjacent arms of the first plurality of arms 454.

In some embodiments, the first iris 450 may be manufactured using one or more of a variety of methods. In some embodiments, the first iris 450 may be machined. In some embodiments, the first iris 450 may be cut using a waterjet. In some embodiments, the first iris 450 may be laser cut. In some embodiments, the first iris 450 may be injection molded. In some embodiments, the first iris 450 may be cast. Other methods of manufacture are also contemplated.

In some embodiments, the device 400 may include a second iris 460 positioned adjacent the housing 410. In at least some embodiments, the second iris 460 may be positioned at least partially within the housing 410. The second iris 460 may include a second circumferential ring 462 extending and/or oriented transverse to the central longitudinal axis. In some embodiments, the second circumferential ring 462 may be generally disc-like in appearance. In some embodiments, the second iris 460 and/or the second circumferential ring 462 may have a substantially circular outer perimeter. In some embodiments, the second iris 460 and/or the second circumferential ring 462 of the second iris 460 may be configured to engage and/or may abut the first end of the loading funnel 420 when the loading funnel 420 is engaged with the housing 410.

The second iris 460 may include a second plurality of arms 464 extending from the second circumferential ring 462 parallel to the central longitudinal axis. In some embodiments, the second plurality of arms 464 may be fixedly attached to the second circumferential ring 462. In some embodiments, the second plurality of arms 464 may be fixedly attached directly to the second circumferential ring 462. In some embodiments, the second plurality of arms 464 may extend from the second circumferential ring 462 in a second direction parallel to the central longitudinal axis. In some embodiments, the second direction may be away from the first threaded member 430 and/or toward from the loading funnel 420. Other configurations are also contemplated.

In some embodiments, the second plurality of arms 464 of the second iris 460 may define a second central opening 466 positioned coaxially relative to the central longitudinal axis. In some embodiments, each of the second plurality of arms 464 of the second iris 460 may include a second tapered surface 468. In some embodiments, the second tapered surface 468 may taper radially inward as the second tapered surface 468 extends away from the second circumferential ring 462. In some embodiments, the second tapered surface 468 may taper radially inward in the second direction. Other configurations are also contemplated. In some embodiments, the second central opening 466 may be coaxial with and/or may be coaxially aligned with a first opening 424 formed in the first end of the loading funnel 420.

In at least some embodiments, the second plurality of arms 464 may be integrally and/or monolithically formed with the second circumferential ring 462 from a single piece of material. Some suitable but non-limiting examples of materials that may be used to form the second iris 460, including but not limited to metals and metal alloys, composites, ceramics, polymers, and the like, are described below. In a preferred embodiment, the second iris 460 and/or the single piece of material is formed from a polymeric material. In at least some embodiments, the second iris 460 may be formed from the same material as the first iris 450. Other configurations are also contemplated. In at least some embodiments, the second plurality of arms 464 may be configured to resiliently flex, deflect, and/or bend to permit relative movement between adjacent arms of the second plurality of arms 464.

In some embodiments, the second iris 460 may be manufactured using one or more of a variety of methods. In some embodiments, the second iris 460 may be machined. In some embodiments, the second iris 460 may be cut using a waterjet. In some embodiments, the second iris 460 may be laser cut. In some embodiments, the second iris 460 may be injection molded. In some embodiments, the second iris 460 may be cast. Other methods of manufacture are also contemplated.

In some embodiments, the device 400 may include a compressor element 470 disposed between the second iris 460 and the second threaded member 440. In some embodiments, the compressor element 470 may be disposed between the second iris 460 and the housing 410. In some embodiments, a first portion 472 of the compressor element 470 may be disposed radially outward of the housing 410. In some embodiments, a second portion 474 of the compressor element 470 may be disposed radially inward of the housing 410. The compressor element 470 may be movable relative to the housing 410. In some embodiments, the compressor element 470 may be axially movable relative to the housing 410. Some suitable but non-limiting examples of materials that may be used to form the compressor element 470, including but not limited to metals and metal alloys, composites, ceramics, polymers, and the like, are described below.

In some embodiments, the compressor element 470 may be manufactured using one or more of a variety of methods. In some embodiments, the compressor element 470 may be machined. In some embodiments, the compressor element 470 may be cut using a waterjet. In some embodiments, the compressor element 470 may be laser cut. In some embodiments, the compressor element 470 may be injection molded. In some embodiments, the compressor element 470 may be cast. Other methods of manufacture are also contemplated.

In some embodiments, the device 400 may include a cover plate 480 positioned adjacent the housing 410. In some embodiments, the cover plate 480 may be releasably secured to the housing 410. In some embodiments, the cover plate 480 may be releasably secured to the housing 410 over the compressor element 470. In some embodiments, the cover plate 480 may releasably secure the compressor element 470 to and/or at least partially within the housing 410. In at least some embodiments, the cover plate 480 may be releasably secured to the housing 410 using mechanical fasteners. In some embodiments, the cover plate 480 may be releasably secured to the housing 410 using a threaded engagement, a tab and slot system, or other suitable means of securement. Other configurations and/or combinations thereof are also contemplated. In some embodiments, the cover plate 480 may be configured to secure the compressor element 470 to the housing 410 such that the first portion 472 of the compressor element 470 is disposed radially outward of the housing 410 and the second portion 474 of the compressor element 470 is disposed radially inward of the housing 410. Some suitable but non-limiting examples of materials that may be used to form the cover plate 480, including but not limited to metals and metal alloys, composites, ceramics, polymers, and the like, are described below.

In at least some embodiments, the first threaded member 430 configured to rotatably and/or threadably engage the cover plate 480. In some embodiments, the cover plate 480 may include external threads configured to engage with internal threads formed in the first threaded member 430. In some embodiments, the cover plate 480 may have an outer radial extent that is less than an outer radial extent of the housing 410. Other configurations are also contemplated.

In some embodiments, the second iris 460 may be axially offset from the first iris 450. In some embodiments, the second iris 460 may be axially spaced apart from the first iris 450. In some embodiments, the cover plate 480 may be disposed between the first iris 450 and the second iris 460. In some embodiments, the first iris 450 and/or the first circumferential ring 452 of the first iris 450 may engage and/or abut the cover plate 480. In some embodiments, the second iris 460 and/or the second circumferential ring 462 of the second iris 460 may engage and/or abut the cover plate 480. Alternatively, in some embodiments, the second iris 460 may be disposed adjacent to the first iris 450. In some embodiments, the second iris 460 may be configured to engage the cover plate 480. In some embodiments, the second iris 460 may abut the first iris 450. In some embodiments, the second circumferential ring 462 of the second iris 460 may abut the first circumferential ring 452 of the first iris 450. Other configurations are also contemplated.

In some embodiments, the device may include a star pusher similar to and/or the same as the star pusher 190 described above (e.g., FIG. 2), wherein the star pusher may be configured to translate axially along the loading funnel 420 and a star pusher nut similar to and/or the same as the star pusher nut 198 described above (e.g., FIG. 2), wherein the star pusher nut may be configured to engage the loading funnel 420. The star pusher nut may be configured to rotatably and/or threadably engage the loading funnel 420. In some embodiments, the loading funnel 420 may include external threads configured to receive internal threads formed in the star pusher nut. The star pusher nut may be configured to rotate relative to the loading funnel 420. The star pusher nut may be configured to translate axially relative to the loading funnel 420. In at least some embodiments, rotation of the star pusher nut relative to the loading funnel 420 when the star pusher nut is engaged with the loading funnel 420 may translate the star pusher nut axially along and/or relative to the loading funnel 420. Some suitable but non-limiting examples of materials that may be used to form the star pusher and/or the star pusher nut, including but not limited to metals and metal alloys, composites, ceramics, polymers, and the like, are described below.

In some embodiments, the star pusher nut may be configured to engage the star pusher. In some embodiments, the star pusher nut may be configured to translate the star pusher along and/or relative to the loading funnel 420. In some embodiments, the start pusher nut may be configured to translate the star pusher axially along and/or relative to the loading funnel 420. In some embodiments, the star pusher nut may be configured to translate the star pusher along and/or relative to the loading funnel 420 as the star pusher nut is rotated relative to the loading funnel 420. In some embodiments, the star pusher nut may be configured to translate the star pusher axially along and/or relative to the loading funnel 420 as the star pusher nut is rotated relative to the loading funnel 420.

Similar to above, the star pusher may include an outer ring and a plurality of legs extending radially inward from the outer ring. The plurality of legs may be configured to be disposed in and/or to project through a plurality of longitudinal slots formed through a side wall of the loading funnel 420. As such, the star pusher may be non-rotatable relative to the loading funnel 420 when the star pusher is engaged with the loading funnel 420. The star pusher may be adapted and/or configured to push and/or translate a stent axially along, relative to, and/or through the loading funnel 420 as the star pusher is translated axially along and/or relative to the loading funnel 420. In at least some embodiments, the stent may be a component of and/or may be included in a medical implant. In some embodiments, the medical implant may include and/or may be a replacement heart valve implant.

The first threaded member 430 may be configured to rotatably and/or threadably engage the housing 410 and/or the cover plate 480. In some embodiments, the first threaded member 430 may be configured to engage the first plurality of arms 454 of the first iris 450. In some embodiments, rotation of the first threaded member 430 relative to the housing 410 may change a size of the first central opening 456 of the first iris 450. In some embodiments, the first plurality of arms 454 of the first iris 450 may be configured to deflect radially between a first configuration and a second configuration upon rotation of the first threaded member 430 relative to the housing 410 and/or the cover plate 480. In at least some embodiments, the first plurality of arms 454 of the first iris 450 may be self-biased toward the first configuration. In some embodiments, the first central opening 456 of the first iris 450 may have a first size in the first configuration and a second size in the second configuration less than the first size.

In some embodiments, the first threaded member 430 may include a first angled surface 432 (e.g., FIG. 9) defining a first central aperture 434 of the first threaded member 430. In some embodiments, the first tapered surface 458 of the first plurality of arms 454 of the first iris 450 may be configured to engage the first angled surface 432 of the first threaded member 430 as the first threaded member 430 is rotated relative to the housing 410 and/or the cover plate 480.

In some embodiments, the first plurality of arms 454 of the first iris 450 may be configured to deflect radially inward from the first configuration toward the second configuration upon rotation of the first threaded member 430 relative to the housing 410 and/or the cover plate 480. In some embodiments, the first plurality of arms 454 of the first iris 450 may be configured to deflect radially inward from the first configuration toward the second configuration upon clockwise rotation of the first threaded member 430 relative to the housing 410 and/or the cover plate 480. Other configurations are also contemplated.

In some embodiments, the first plurality of arms 454 of the first iris 450 may be configured to deflect radially outward from the second configuration toward the first configuration upon rotation of the first threaded member 430 relative to the housing 410 and/or the cover plate 480. In some embodiments, the first plurality of arms 454 of the first iris 450 may be configured to deflect radially outward from the second configuration toward the first configuration upon counterclockwise rotation of the first threaded member 430 relative to the housing 410 and/or the cover plate 480. Other configurations are also contemplated.

The second threaded member 440 may be configured to rotatably and/or threadably engage the housing 410. In some embodiments, the second threaded member 440 may be configured to engage the compressor element 470 and the compressor element 470 may be configured to engage the second plurality of arms 464 of the second iris 460. In some embodiments, the second threaded member 440 may be configured to engage the first portion 472 of the compressor element 470 and the compressor element 470 may be configured to engage the second plurality of arms 464 of the second iris 460 as the second threaded member 440 is rotated relative to the housing 410. In some embodiments, the compressor element 470 may be axially translated relative to the housing 410 and/or the cover plate 480 via rotation of the second threaded member 440 relative to the housing 410. In some embodiments, the compressor element 470 may be axially translated towards the first iris 450, the first threaded member 430, and/or the cover plate 480 via rotation of the second threaded member 440 relative to the housing 410.

In some embodiments, rotation of the second threaded member 440 relative to the housing 410 may change a size of the second central opening 466 of the second iris 460. In some embodiments, the second plurality of arms 464 of the second iris 460 may be configured to deflect radially between a first configuration and a second configuration upon rotation of the second threaded member 440 relative to the housing 410. In at least some embodiments, the second plurality of arms 464 of the second iris 460 may be self-biased toward the first configuration. In some embodiments, the second central opening 466 of the second iris 460 may have a first size in the first configuration and a second size in the second configuration less than the first size.

In some embodiments, the compressor element 470 may include a second angled surface 476 (e.g., FIG. 9) defining a second central aperture 478 of the compressor element 470. In some embodiments, the second tapered surface 468 of the second plurality of arms 464 of the second iris 460 may be configured to engage the second angled surface 476 of the compressor element 470 as the second threaded member 440 is rotated relative to the housing 410.

In some embodiments, the second plurality of arms 464 of the second iris 460 may be configured to deflect radially inward from the first configuration toward the second configuration upon rotation of the second threaded member 440 relative to the housing 410. In some embodiments, the second plurality of arms 464 of the second iris 460 may be configured to deflect radially inward from the first configuration toward the second configuration upon clockwise rotation of the second threaded member 440 relative to the housing 410. In some embodiments, the housing 410 and/or the second threaded member 440 may include left-handed threads. In some embodiments, clockwise rotation of the second threaded member 440 relative to the housing 410 may translate the second threaded member 440 and/or the compressor element 470 towards the first threaded member 430 and/or away from the loading funnel 420. Other configurations are also contemplated.

In some embodiments, the second plurality of arms 464 of the second iris 460 may be configured to deflect radially outward from the second configuration toward the first configuration upon rotation of the second threaded member 440 relative to the housing 410. In some embodiments, the second plurality of arms 464 of the second iris 460 may be configured to deflect radially outward from the second configuration toward the first configuration upon counterclockwise rotation of the second threaded member 440 relative to the housing 410. Other configurations are also contemplated.

In some embodiments, the first threaded member 430 and the second threaded member 440 may be configured to rotate relative to the housing 410 independently of each other. In some embodiments, the first threaded member 430 may be movable relative to the housing 410 independently of the second threaded member 440. In some embodiments, the second threaded member 440 may be movable relative to the housing 410 independently of the first threaded member 430.

In some embodiments, the first threaded member 430 and the second threaded member 440 may be movable relative to the housing 410 together, in tandem, and/or simultaneously. In some embodiments, the first threaded member 430 and the second threaded member 440 may be movable relative to the housing 410 together, in tandem, and/or simultaneously at one time, in one direction, or during a particular step of a method disclosed herein, and the first threaded member 430 and the second threaded member 440 may be movable relative to the housing 410 independently of each other at another time, in another direction, or during another particular step of a method disclosed herein. Other configurations are also contemplated.

FIGS. 10-13 are cross-sectional views of the device 400 showing selected aspects of a method of radially compressing the stent 200. The device 400 may generally include elements and/or features as described herein. For improved clarity and understanding, some elements or features of the device 400 and/or the stent 200 are not shown or are not shown in their entirety. In some instances, reference numbers discussed in the context of FIGS. 10-13 may not be shown, and the reader may refer back to FIGS. 8-9.

Figure 10:
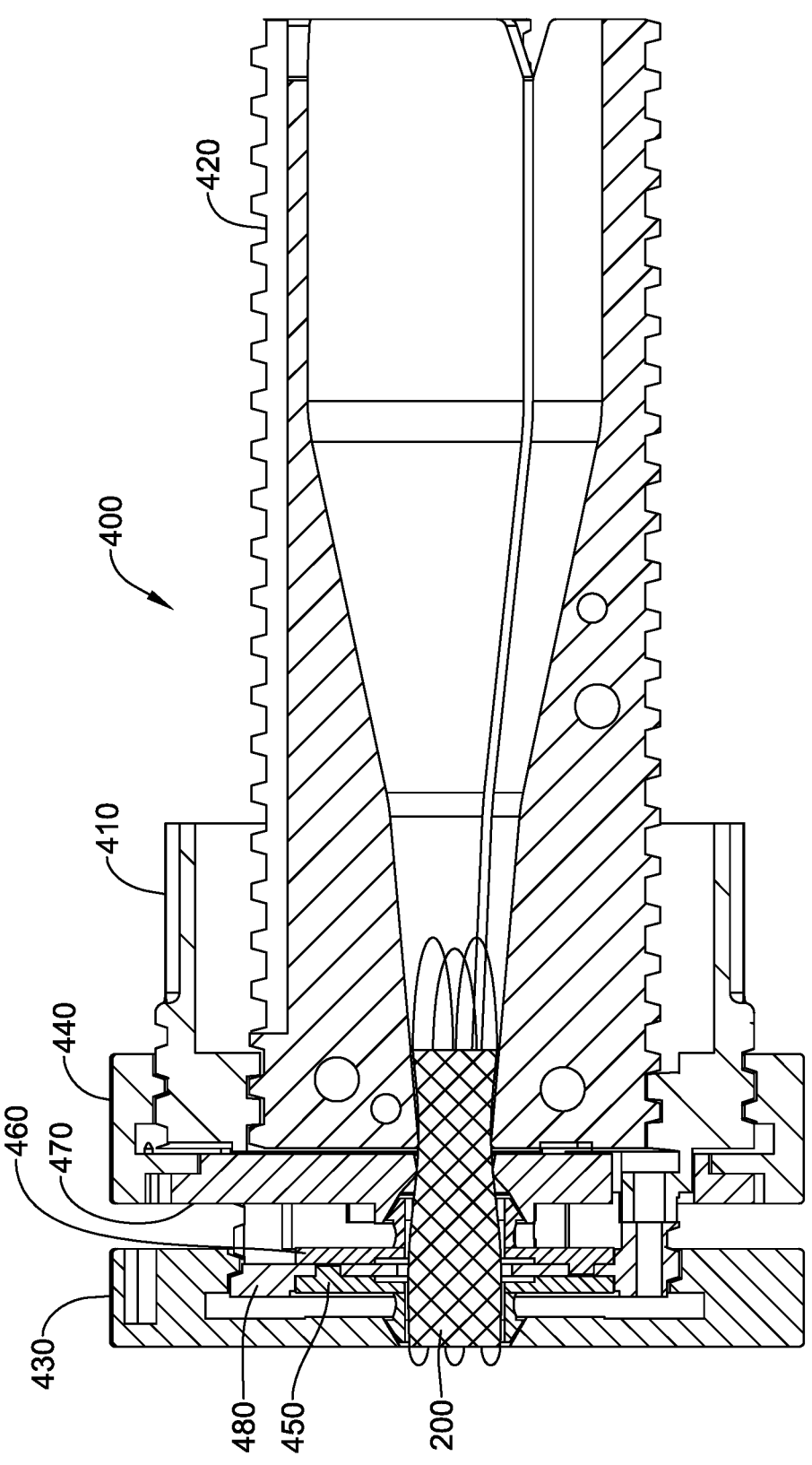
FIGS. 10-13 are partial cross-sectional views illustrating selected aspects of a method of radially compressing a stent using the device of FIGS. 8-9.

A method of radially compressing a stent may include inserting a stent 200 in a first configuration through the loading funnel 420 removably coupled to the housing 410 into the first central opening 456 of the first iris 450, as seen in FIG. 10. In some embodiments, in the first configuration, the stent 200 may be in an expanded configuration. In some embodiments, in the first configuration, the stent 200 may be in a partially collapsed state. For example, in some embodiments, the device 400 may include the loading funnel 420 adapted to partially collapse the stent 200 as the stent 200 is inserted into the first central opening 456 of the first iris 450. In some embodiments, the loading funnel 420 may be configured to releasably attach to the housing 410, as described herein. For example, in the view shown in FIG. 10, the loading funnel 420 may be configured to be inserted into the housing 410 from the right side of the view until at least a portion of the loading funnel 420 is positioned adjacent to and/or is engaged with the housing 410. In some embodiments, the method may include inserting the stent 200 into and/or through the loading funnel 420 before inserting the stent 200 in the first configuration into first central opening 456 of the first iris 450.

In some embodiments, inserting the stent 200 may include advancing the stent 200 through the loading funnel 420 using the star pusher and the star pusher nut. In some embodiments, as the star pusher nut is rotated relative to the loading funnel 420, the star pusher nut translates axially along the loading funnel 420. As the star pusher nut translates along the loading funnel 420, the star pusher is similarly translated along the loading funnel 420 to push the stent 200 axially within and/or through the loading funnel 420.

In some embodiments, the method may include inserting the stent 200 in the first configuration into the second central opening 466 of the second iris 460 axially offset from the first iris 450. In some embodiments, the method may include inserting the stent 200 through the second central aperture 478 of the compressor element 470 and/or the cover plate 480. In some embodiments, the method may include inserting the stent 200 through the second central aperture 478 of the compressor element 470 and/or the cover plate 480 before inserting the stent 200 into the first central opening 456 of the first iris 450. Other configurations are also contemplated.

Figure 11:
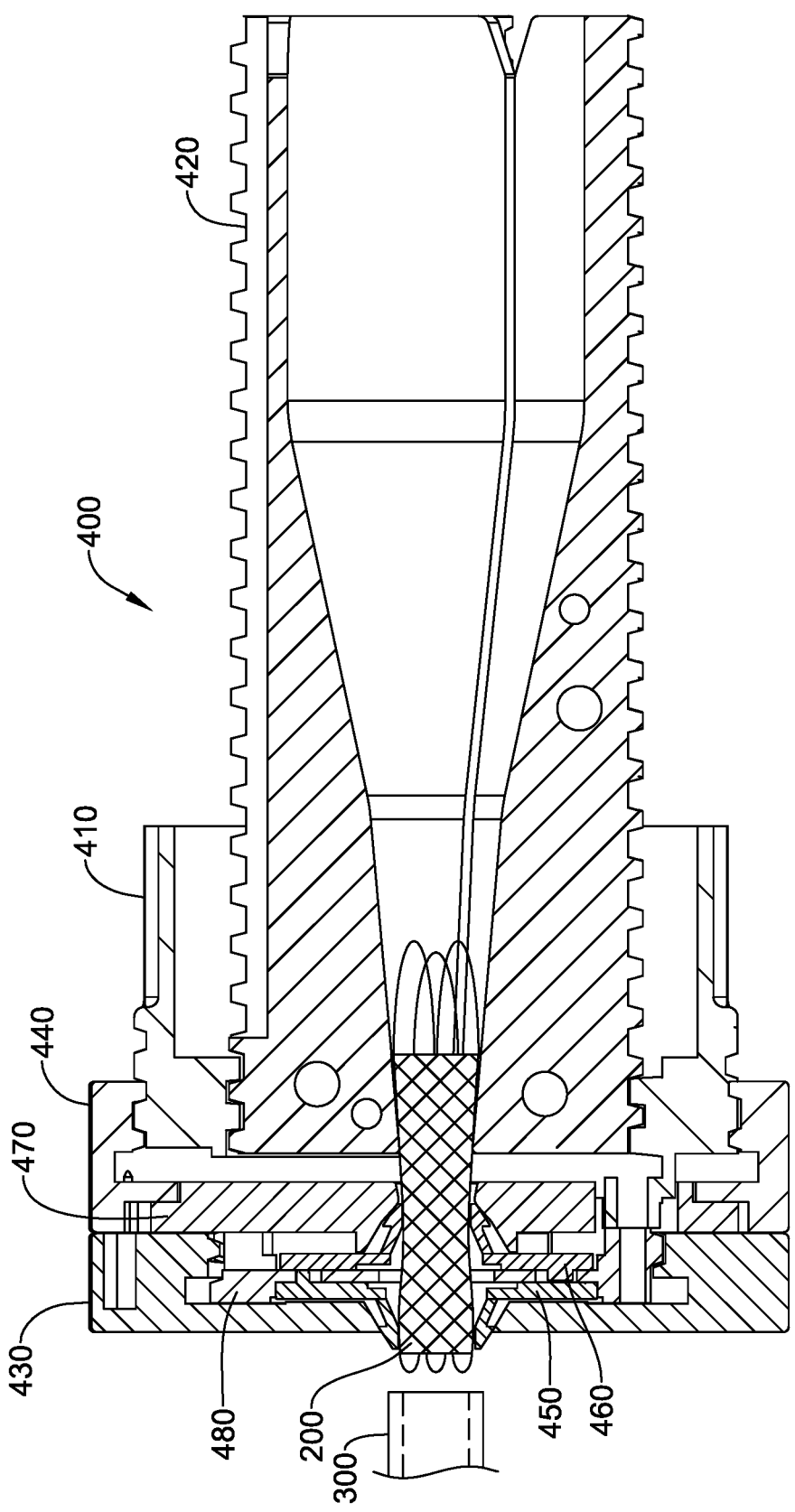

The method may include rotating the first threaded member 430 relative to the housing 410, the cover plate 480, and/or the first iris 450 to shift the first plurality of arms 454 of the first iris 450 from the first configuration toward and/or to the second configuration, as seen in FIG. 11, wherein the first central opening 456 has a first size in the first configuration (e.g., FIG. 10) and a second size in the second configuration less than the first size (e.g., FIG. 11). In some embodiments, the method may include rotating the first threaded member 430 clockwise relative to the housing 410 and/or the cover plate 480 to shift the first plurality of arms 454 of the first iris 450 from the first configuration toward and/or to the second configuration. In the second configuration of the first plurality of arms 454 of the first iris 450, a first portion of the stent 200 disposed within the first iris 450 and/or the first central opening 456 of the first iris 450 may be in a radially compressed configuration.

In some embodiments, the method may include rotating the second threaded member 440 relative to the housing 410 and/or the cover plate 480 to shift the second plurality of arms 464 of the second iris 460 from a first configuration toward and/or to a second configuration, wherein the second central opening 466 has a first size in the first configuration (e.g., FIG. 10) and a second size in the second configuration (e.g., FIG. 11) less than the first size. In some embodiments, the method may include rotating the second threaded member 440 clockwise relative to the housing 410 and/or the cover plate 480 to shift the second plurality of arms 464 of the second iris 460 from the first configuration toward and/or to the second configuration. In the second configuration of the second plurality of arms 464 of the second iris 460, a second portion of the stent 200 disposed within the second iris 460 and/or the second central opening 466 of the second iris 460 may be in the radially compressed configuration.

Figure 12:
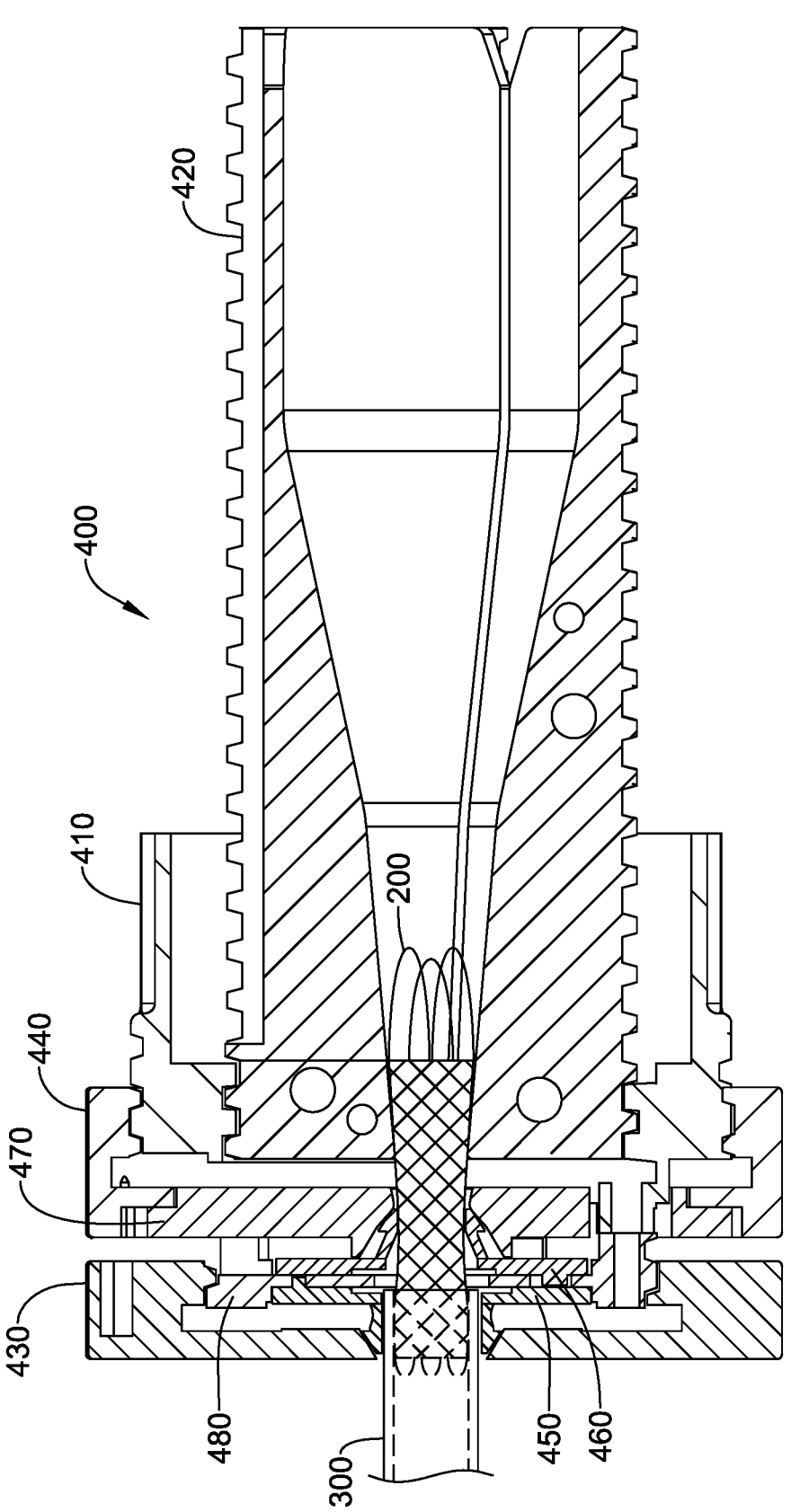

In some embodiments, the method may include positioning a sheath 300 proximate the first iris 450 with the first plurality of arms 454 in the second configuration and the first portion of the stent 200 disposed within the first iris 450 and/or the first central opening 456 in the radially compressed configuration, as seen in FIG. 11. After positioning the sheath 300 proximate the first iris 450, the method may include rotating the first threaded member 430 relative to the housing 410 and/or the cover plate 480 to shift the first plurality of arms 454 from the second configuration toward and/or to the first configuration. In some embodiments, the method may include rotating the first threaded member 430 counterclockwise relative to the housing 410 and/or the cover plate 480 to shift the first plurality of arms 454 from the second configuration to the first configuration. The method may further include moving the sheath 300 into the first iris 450 over the stent 200 in the compressed configuration such that the first portion of the stent 200 that was disposed within the first iris 450 is disposed within a lumen of the sheath 300, as seen in FIG. 12. In some embodiments, the sheath 300 has an inner diameter less than an outer diameter of the stent 200 in the first configuration. As such, radial compression of the stent 200 is required in order to move the stent 200 into the lumen of the sheath 300.

Figure 13:
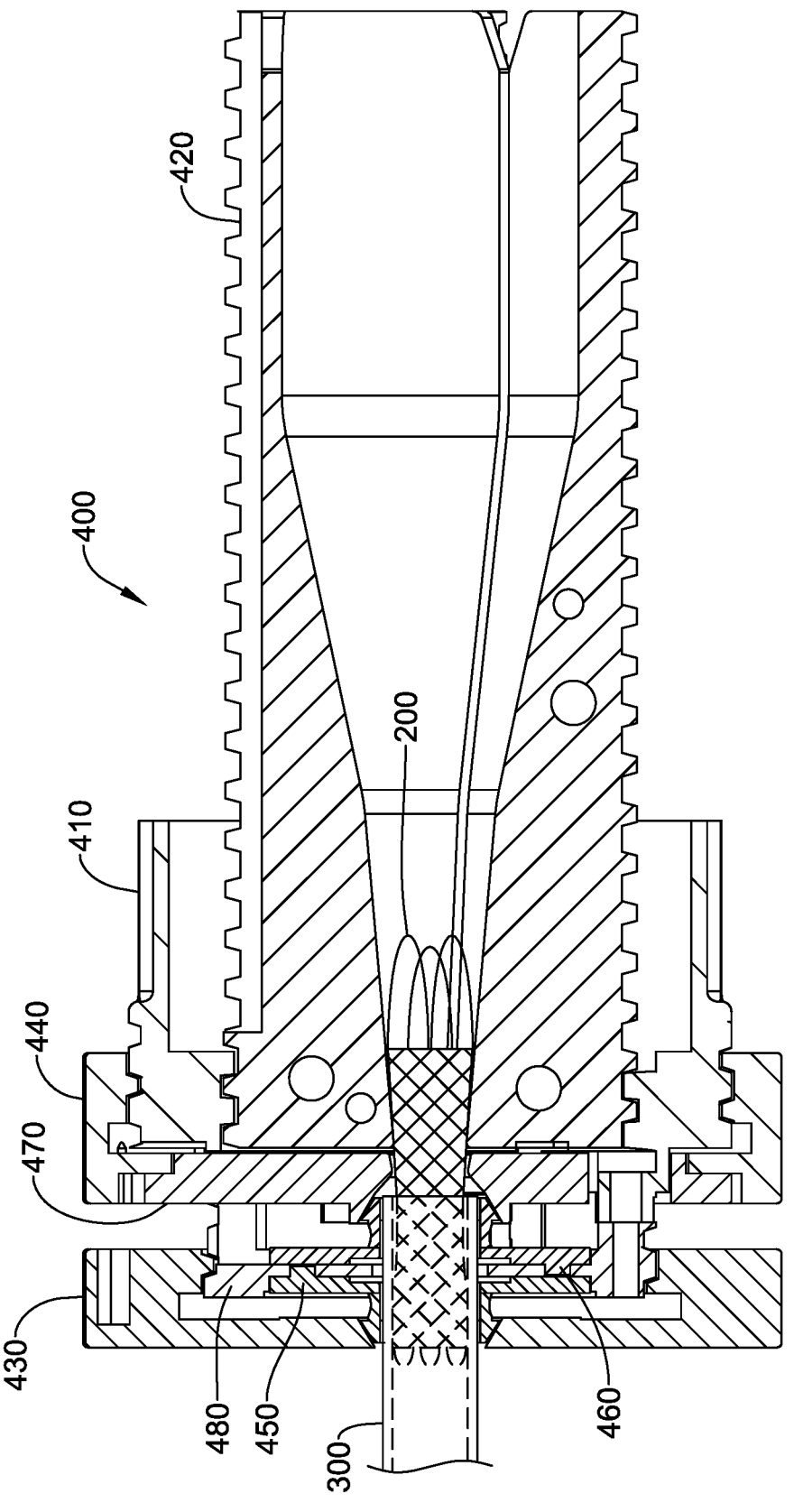

In some embodiments, after moving the sheath 300 into the first iris 450 over the stent 200, the method may further include rotating the second threaded member 440 relative to the housing 410 and/or the cover plate 480 to shift the second plurality of arms 464 of the second iris 460 from the second configuration toward and/or to the first configuration. In some embodiments, the method may include rotating the second threaded member 440 counterclockwise relative to the housing 410 and/or the cover plate 480 to shift the second plurality of arms 464 of the second iris 460 from the second configuration toward and/or to the first configuration. The method may further include moving the sheath 300 into the second iris 460 over the stent 200 in the compressed configuration such that the second portion of the stent 200 that was disposed within the second iris 460 is disposed within the lumen of the sheath 300, as seen in FIG. 13.

In some embodiments, the device 100 may permit the stent 200 to be loaded into the sheath 300 without moving or advancing the stent 200 through the device 400 multiple times, thereby reducing the number of steps required to sheath the stent 200, reducing or eliminating multiple compression steps, and/or reducing opportunity for damage to the stent 200. In some embodiments, the device 400 may be reusable following suitable sterilization techniques. In some embodiments, the device 400 may be disposable and/or may be classified or used as a single-use device.

Additionally, it is contemplated that the device 400 may include additional irises, etc. to accommodate a stent of longer length and/or varying outer diameter (in a first configuration and/or in a compressed configuration). For example, in some embodiments, the second size of the first central opening 456 of the first iris 450 may be the same as the second size of the second central opening 466 of the second iris 460, and additional central openings of additional irises may have a second size that is the same as the second size of the first central opening 456 and/or the second central opening 466. In some embodiments, the second size of the first central opening 456 of the first iris 450 may be different from the second size of the second central opening 466 of the second iris 460, and additional central openings of additional irises may have a second size that is the same as the second size of the first central opening 456 and the second central opening 466, the additional central openings of additional irises may have a second size that is the same as the second size of one of the first central opening 456 and the second central opening 466, or the additional central openings of additional irises may have a second size that is the different from the second size of the first central opening 456 and the second central opening 466. Other configurations are also contemplated.

In some embodiments, wherein the device 400 includes additional irises, the process described above with respect to moving the sheath 300 into the first iris 450 and the second iris 460 may be repeated as necessary to move the sheath 300 over additional portions of the stent 200 disposed within those irises.

Additionally, in some embodiments, if additional length of the stent 200 needs to be moved into the sheath 300, the stent 200 may be advanced through the loading funnel 420 into the first iris 450 and the second iris 460, and the first iris 450 and the second iris 460 may be again shifted from the first configuration to the second configuration and the process may be repeated.

In some embodiments, after moving the sheath 300 into the second iris 460 over the stent 200 such that the second portion of the stent 200 that was disposed within the second iris 460 is disposed within the lumen of the sheath 300, the sheath 300 and the first and second portions of the stent 200 that were disposed within the first and second irises, respectively, may be advanced through the housing 410 and/or the loading funnel 420, and a separate sheath may be translated over an uncovered portion of the stent 200 toward the sheath 300 to cover at least some of the uncovered portion of the stent 200 that remains outside of the sheath 300. Other configurations are also contemplated.

The materials that can be used for the various components of the device and the various elements thereof disclosed herein may include those commonly associated with medical devices and devices used and/or associated with medical devices. For simplicity purposes, the following discussion refers to the system. However, this is not intended to limit the devices and methods described herein, as the discussion may be applied to other elements, members, components, or devices disclosed herein, such as, but not limited to, the stent, the expandable framework, the first and/or second plurality of arms, the circumferential ring(s), the housing, etc. and/or elements or components thereof.

In some embodiments, the system and/or components thereof may be made from a metal, metal alloy, polymer (some examples of which are disclosed below), a metal-polymer composite, ceramics, combinations thereof, and the like, or other suitable material.

Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), MARLEX® high-density polyethylene, MARLEX® low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro (propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, polyisobutylene (PIB), polyisobutylene polyurethane (PIBU), polyurethane silicone copolymers (for example, Elast-Eon® from AorTech Biomaterials or ChronoSil® from AdvanSource Biomaterials), ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; platinum; palladium; gold; combinations thereof; or any other suitable material.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. A device for radially compressing a stent, comprising:
   a housing extending along a central longitudinal axis;
   a first threaded member configured to engage the housing;

a second threaded member configured to engage the housing;

a first iris positioned adjacent the housing;

a second iris positioned adjacent the housing; and a compressor element disposed between the second iris and the second threaded member;

wherein the first iris includes a first circumferential ring extending transverse to the central longitudinal axis and a first plurality of arms extending from the first circumferential ring in a first direction parallel to the central longitudinal axis;

wherein the first plurality of arms defines a first central opening positioned coaxially relative to the central longitudinal axis;

wherein rotation of the first threaded member relative to the housing changes a size of the first central opening;

wherein the second iris includes a second circumferential ring extending transverse to the central longitudinal axis and a second plurality of arms extending from the second circumferential ring in a second direction parallel to the central longitudinal axis;

wherein the second plurality of arms defines a second central opening positioned coaxially relative to the central longitudinal axis;

wherein rotation of the second threaded member relative to the housing changes a size of the second central opening.

2. The device of claim 1, wherein the second threaded member is configured to engage the compressor element and the compressor element is configured to engage the second plurality of arms.

3. The device of claim 1, wherein each of the second plurality of arms includes a second tapered surface configured to engage a second angled surface defining a second central aperture of the compressor element.

4. The device of claim 1, wherein the second iris is axially offset from the first iris.

5. The device of claim 1, wherein the first threaded member and the second threaded member are rotatable relative to the housing independently of each other.

6. The device of claim 1, wherein a first portion of the compressor element is disposed radially outward of the housing and a second portion of the compressor element is disposed radially inward of the housing.

7. A method of radially compressing a stent, comprising:

inserting a stent in a first configuration through a loading funnel removably coupled to a housing into a first central opening of a first iris positioned adjacent the housing;

wherein the first iris includes a first circumferential ring extending transverse to a central longitudinal axis of the housing, and a first plurality of arms extending from the first circumferential ring in a first direction parallel to the central longitudinal axis and defining the first central opening; and rotating a first threaded member relative to the housing to shift the first plurality of arms from a first configuration to a second configuration, wherein the first central opening has a first size in the first configuration and a second size in the second configuration less than the first size;

wherein in the second configuration of the first plurality of arms, a first portion of the stent disposed within the first iris is in a radially compressed configuration.

8. The method of claim 7, further comprising:

positioning a sheath proximate the first iris with the first plurality of arms in the second configuration and the first portion of the stent disposed within the first iris in the radially compressed configuration;

rotating the first threaded member relative to the housing to shift the first plurality of arms from the second configuration to the first configuration; and moving the sheath into the first iris over the stent such that the first portion of the stent that was disposed within the first iris is disposed within the sheath.

9. The method of claim 8, wherein the sheath has an inner diameter less than an outer diameter of the stent in the first configuration.

10. The method of claim 7, wherein inserting the stent further includes inserting the stent in the first configuration into the first iris and a second iris axially offset from the first iris, wherein the second iris includes a second circumferential ring extending transverse to the central longitudinal axis and a second plurality of arms extending from the second circumferential ring in a second direction parallel to the central longitudinal axis and defining a second central opening.

11. The method of claim 10, further comprising:

rotating a second threaded member relative to the housing to shift the second plurality of arms from a first configuration to a second configuration, wherein the second central opening has a first size in the first configuration and a second size in the second configuration less than the first size;

wherein in the second configuration of the second plurality of arms, a second portion of the stent disposed within the second iris is in the radially compressed configuration.

12. The method of claim 11, further comprising:

positioning a sheath proximate the first iris with the first plurality of arms in the second configuration and the first portion of the stent disposed within the first iris in the radially compressed configuration;

rotating the first threaded member relative to the housing to shift the first plurality of arms from the second configuration to the first configuration;

moving the sheath into the first iris over the stent such that the first portion of the stent that was disposed within the first iris is disposed within the sheath;

rotating the second threaded member relative to the housing to shift the second plurality of arms from the second configuration to the first configuration; and moving the sheath into the second iris over the stent such that the second portion of the stent that was disposed within the second iris is disposed within the sheath.

* * * * *